United States Patent
Irving et al.

(10) Patent No.: US 12,283,376 B2
(45) Date of Patent: Apr. 22, 2025

(54) SYSTEMS AND METHODS TO MONITOR PATIENT DEVICES

(71) Applicant: Murj, Inc., Santa Cruz, CA (US)

(72) Inventors: Christopher S. Irving, Santa Cruz, CA (US); Mark A. Pederson, Los Altos, CA (US)

(73) Assignee: Murj, Inc., Santa Cruz, CA (US)

( * ) Notice: Subject to any disclaimer, the term of this patent is extended or adjusted under 35 U.S.C. 154(b) by 182 days.

(21) Appl. No.: 17/659,815

(22) Filed: Apr. 19, 2022

(65) Prior Publication Data
US 2023/0335273 A1    Oct. 19, 2023

(51) Int. Cl.
*G16H 40/67* (2018.01)
*G16H 15/00* (2018.01)
(Continued)

(52) U.S. Cl.
CPC .............. *G16H 40/67* (2018.01); *G16H 15/00* (2018.01); *G16H 20/00* (2018.01); *H04W 4/80* (2018.02)

(58) Field of Classification Search
CPC ........ G16H 40/67; G16H 15/00; G16H 20/00; G16H 20/10; G16H 20/40; G16H 50/30; H04W 4/80
(Continued)

(56) References Cited

U.S. PATENT DOCUMENTS 4,173,971 A  11/1979  Karz
4,783,803 A  11/1988  Baker et al.
(Continued)

FOREIGN PATENT DOCUMENTS

JP  2001101306 A  4/2001
JP  2005063253 A  3/2005
(Continued)

OTHER PUBLICATIONS

Van der Velde et al., "Integration of remote monitoring data into the hospital electronic health record system: Implementation based on international standards," 2011 Computing in Cardiology, 2011, pp. 581-584 (Year: 2011).*

(Continued)

*Primary Examiner* — Joy Chng
(74) *Attorney, Agent, or Firm* — Polsinelli PC

(57) ABSTRACT

Systems and methods include a device management platform for managing a plurality of devices (e.g., for a clinic system). A system can include a patient system such as a patient device (e.g., an implanted cardiac device, a mobile device, etc.) which transmits data to the device management platform and/or a clinic system. The device management platform tracks measured physiological parameters of the patient. Transmission data received from the patient system includes data corresponding to the measured physiological parameters. The device management platform generates a workflow interface at the clinic system based on a care pathway, a billing pathway, and the measured physiological parameters. Additionally, the device management platform can determine an outcome goal value and one or more benchmark values to reach the outcome goal value, and can send action instructions (e.g., to the patient system) based on comparing the measured physiological parameters to the one or more benchmark values.

20 Claims, 12 Drawing Sheets

(51) Int. Cl.
*G16H 20/00* (2018.01)
*H04W 4/80* (2018.01)

(58) Field of Classification Search
USPC .................................................... 705/2–3
See application file for complete search history.

(56) References Cited

U.S. PATENT DOCUMENTS

| | | |
|---|---|---|
| 5,798,752 A | 8/1998 | Buxton et al. |
| D507,798 S | 7/2005 | Jewitt et al. |
| D571,818 S | 6/2008 | Loehr et al. |
| D579,020 S | 10/2008 | Aliaga |
| D606,088 S | 12/2009 | Yokouchi et al. |
| D617,808 S | 6/2010 | Thompson et al. |
| 7,761,507 B2 | 7/2010 | Herf et al. |
| 7,805,199 B2 | 9/2010 | Kenknight et al. |
| 8,060,821 B2 | 11/2011 | Seymour et al. |
| 8,112,151 B1 | 2/2012 | Cogan et al. |
| D694,259 S | 11/2013 | Klein |
| D695,758 S | 12/2013 | Tagliabue et al. |
| D703,688 S | 4/2014 | Choi |
| D731,520 S | 6/2015 | Xiong et al. |
| D732,051 S | 6/2015 | Jeong et al. |
| D741,882 S | 10/2015 | Shmilov et al. |
| D749,623 S | 2/2016 | Gray et al. |
| D753,670 S | 4/2016 | Tian |
| D757,065 S | 5/2016 | Jeon et al. |
| D761,842 S | 7/2016 | Johnson et al. |
| D763,879 S | 8/2016 | Worrell et al. |
| D764,501 S | 8/2016 | Dias et al. |
| D768,707 S | 10/2016 | Gagnier |
| D771,649 S | 11/2016 | Eze et al. |
| D777,177 S | 1/2017 | Chen et al. |
| D777,195 S | 1/2017 | Dain et al. |
| D779,514 S | 2/2017 | Baris et al. |
| D780,797 S | 3/2017 | Kisielius et al. |
| D781,889 S | 3/2017 | Wills et al. |
| D781,905 S | 3/2017 | Nakaguchi et al. |
| D782,526 S | 3/2017 | Rind et al. |
| D783,030 S | 4/2017 | Lee et al. |
| D785,022 S | 4/2017 | Vazquez et al. |
| D788,128 S | 5/2017 | Wada |
| D789,377 S | 6/2017 | Vazquez |
| D789,397 S | 6/2017 | Lee et al. |
| D789,982 S | 6/2017 | Christiana et al. |
| D792,424 S | 7/2017 | Meegan et al. |
| D792,426 S | 7/2017 | Theodore et al. |
| D794,047 S | 8/2017 | Gandhi et al. |
| D796,523 S | 9/2017 | Bhandari et al. |
| D798,320 S | 9/2017 | Gouvernel et al. |
| D800,741 S | 10/2017 | Rhodes |
| D803,845 S | 11/2017 | Arora |
| D805,525 S | 12/2017 | Dascola et al. |
| D806,097 S | 12/2017 | Rahn et al. |
| D807,379 S | 1/2018 | Pahwa et al. |
| D807,385 S | 1/2018 | Olsen et al. |
| D807,900 S | 1/2018 | Raji et al. |
| D807,911 S | 1/2018 | Zhou et al. |
| D808,399 S | 1/2018 | Derby et al. |
| D808,400 S | 1/2018 | Coren |
| D808,981 S | 1/2018 | Hazam et al. |
| D822,678 S | 7/2018 | Wu et al. |
| D823,326 S | 7/2018 | Pinzon Garcia et al. |
| D823,327 S | 7/2018 | Durkan et al. |
| D823,860 S | 7/2018 | Wiffen et al. |
| D829,229 S | 9/2018 | Durkan et al. |
| D830,382 S | 10/2018 | Marohn |
| D832,296 S | 10/2018 | Golden et al. |
| D833,459 S | 11/2018 | Blechschmidt et al. |
| D835,138 S | 12/2018 | Edgington, Jr. |
| D840,426 S | 2/2019 | Dieken et al. |
| D841,017 S | 2/2019 | Bathla |
| D841,675 S | 2/2019 | Hoffman et al. |
| D843,403 S | 3/2019 | Casse et al. |
| D845,973 S | 4/2019 | Jaycobs |
| D845,974 S | 4/2019 | Cooperman et al. |
| D847,165 S | 4/2019 | Kolbenheyer |
| D849,014 S | 5/2019 | Senders |
| D849,029 S | 5/2019 | Cooperman et al. |
| D849,773 S | 5/2019 | Jiang et al. |
| 10,289,660 B2 | 5/2019 | Karunamuni et al. |
| D853,412 S | 7/2019 | Hofner et al. |
| D853,420 S | 7/2019 | Ambrose et al. |
| D854,030 S | 7/2019 | Dascola et al. |
| D854,565 S | 7/2019 | Mclaughlin et al. |
| D860,237 S | 9/2019 | Li et al. |
| D860,239 S | 9/2019 | Lirov et al. |
| D867,389 S | 11/2019 | Jamison et al. |
| D869,488 S | 12/2019 | Storr |
| D870,762 S | 12/2019 | Mendoza Corominas et al. |
| D872,117 S | 1/2020 | Kobayashi et al. |
| D874,486 S | 2/2020 | Ragland et al. |
| D875,747 S | 2/2020 | Iida et al. |
| D875,761 S | 2/2020 | Heffernan et al. |
| D876,454 S | 2/2020 | Knowles et al. |
| D877,167 S | 3/2020 | Knowles et al. |
| D879,112 S | 3/2020 | Hejazi et al. |
| D879,134 S | 3/2020 | Jones |
| D880,513 S | 4/2020 | Wang et al. |
| D881,908 S | 4/2020 | Sunil et al. |
| D881,910 S | 4/2020 | Lin |
| D888,739 S | 6/2020 | Christiana et al. |
| D898,056 S | 10/2020 | Olson |
| D905,734 S | 12/2020 | Christiana et al. |
| D906,358 S | 12/2020 | Christiana et al. |
| D914,040 S | 3/2021 | Butka et al. |
| D924,258 S | 7/2021 | Klimer et al. |
| D949,898 S | 4/2022 | Olson |
| 11,456,072 B1 | 9/2022 | Irving et al. |
| 2001/0039504 A1 | 11/2001 | Linberg et al. |
| 2001/0051765 A1 | 12/2001 | Walker et al. |
| 2002/0056575 A1 | 5/2002 | Keely et al. |
| 2002/0082665 A1 | 6/2002 | Haller et al. |
| 2002/0089547 A1 | 7/2002 | Huapaya |
| 2004/0008224 A1 | 1/2004 | Molander et al. |
| 2004/0071344 A1 | 4/2004 | Lui et al. |
| 2005/0021370 A1 | 1/2005 | Riff et al. |
| 2005/0065445 A1 | 3/2005 | Arzbaecher et al. |
| 2005/0192649 A1 | 9/2005 | Shehadeh et al. |
| 2005/0278140 A1 | 12/2005 | Wang |
| 2007/0016857 A1 | 1/2007 | Polleck et al. |
| 2007/0060797 A1 | 3/2007 | Ball et al. |
| 2007/0135855 A1 | 6/2007 | Foshee et al. |
| 2008/0007570 A1 | 1/2008 | Wessel et al. |
| 2008/0109051 A1 | 5/2008 | Splinter et al. |
| 2009/0062671 A1 | 3/2009 | Brockway et al. |
| 2009/0187426 A1 | 7/2009 | Kerstna et al. |
| 2010/0005411 A1 | 1/2010 | Duncker et al. |
| 2010/0114993 A1 | 5/2010 | Holschbach et al. |
| 2010/0134353 A1 | 6/2010 | Van Diggelen |
| 2011/0004277 A1 | 1/2011 | Johnson et al. |
| 2011/0054264 A1 | 3/2011 | Fischell et al. |
| 2011/0106669 A1 | 5/2011 | Baghdassarian |
| 2011/0119212 A1 | 5/2011 | De Bruin et al. |
| 2012/0095300 A1 | 4/2012 | McNair |
| 2012/0141964 A1 | 6/2012 | Lee |
| 2012/0143017 A1 | 6/2012 | Snyder |
| 2012/0194558 A1 | 8/2012 | Dykes et al. |
| 2012/0223889 A1 | 9/2012 | Medlock et al. |
| 2012/0288881 A1 | 11/2012 | Liu |
| 2012/0290599 A1 | 11/2012 | Tian et al. |
| 2013/0035209 A1 | 2/2013 | Gilley et al. |
| 2013/0124186 A1 | 5/2013 | Donabedian et al. |
| 2013/0232437 A1 | 9/2013 | Kim |
| 2013/0274705 A1 | 10/2013 | Burnes et al. |
| 2013/0317852 A1 | 11/2013 | Worrell et al. |
| 2015/0005598 A1* | 1/2015 | Muir .................. A61B 5/7282 |
| | | 600/323 |
| 2015/0227691 A1 | 8/2015 | Bhattacharya et al. |
| 2015/0295914 A1 | 10/2015 | Kelishadi |
| 2015/0324549 A1 | 11/2015 | Nearhood et al. |
| 2015/0370920 A1 | 12/2015 | Van Os et al. |
| 2016/0092641 A1* | 3/2016 | Delaney ............... G16H 40/20 |
| | | 705/3 |

(56) References Cited

U.S. PATENT DOCUMENTS

| | | | |
|---|---|---|---|
| 2016/0246931 A1 | 8/2016 | Rajan et al. | |
| 2016/0292456 A1 | 10/2016 | Dubey et al. | |
| 2016/0306929 A1 | 10/2016 | Butka et al. | |
| 2017/0004260 A1* | 1/2017 | Moturu | G16H 10/60 |
| 2017/0262605 A1 | 9/2017 | Wadhwa et al. | |
| 2017/0312534 A1 | 11/2017 | Cao et al. | |
| 2019/0026838 A1 | 1/2019 | Tan et al. | |
| 2019/0083030 A1 | 3/2019 | Thakur et al. | |
| 2019/0109757 A1 | 4/2019 | Oliveira et al. | |
| 2019/0213544 A1 | 7/2019 | Spirig et al. | |
| 2020/0302825 A1* | 9/2020 | Sachs | A61M 21/00 |
| 2022/0084645 A1* | 3/2022 | Ginsburg | G16H 10/60 |
| 2022/0144427 A1 | 5/2022 | Vernon et al. | |
| 2022/0280047 A1 | 9/2022 | Stadler et al. | |
| 2022/0296906 A1 | 9/2022 | Westphal et al. | |

FOREIGN PATENT DOCUMENTS

| | | | |
|---|---|---|---|
| JP | 2005319151 A | 11/2005 | |
| JP | 2021506039 A | 2/2021 | |
| WO | WO-2010051175 A1 | 5/2010 | |

OTHER PUBLICATIONS

Dec. 27, 2022—(US) Non-Final Office Action—U.S. Appl. No. 17/809,509, 24 pages.

Feb. 1, 2024—(US) Non-Final Office Action—U.S. Appl. No. 16/889,210, 28 Pages.

ANGI71., "Vector Buttons Blue and White," May 17, 2008, Retrieved from the Internet: URL: https://www.istockphoto.com/vector/vector-buttons-blue-and-white-gray-gm95492721-6143274 , 5 pages.

E. T. van der Velde, H. Foeken, T. Witteman, L. van Erven and M. J. Schalij, "Integration of remote monitoring data into the hospital electronic health record system: Implementation based on international standards," 2011 Computing in Cardiology, 2011, pp. 581-584 (Year: 2011).

International Search Report and Written Opinion, PCT/US2016/028470, dated Jul. 22, 2016, 10 pages.

International Search Report and Written Opinion—PCT/US2022/073231, Sep. 27, 2022, 9 pgs.

JP Office Action, JP2020-548891_Aug. 31, 2021.

Notice of Allowance for U.S Appl. No. 15/134,130, mailed on Feb. 21, 2019, 8 pages.

Notice of Allowance for U.S. Appl. No. 17/654,949, mailed on May 9, 2022, 8 pages.

Notice of Allowance for U.S. Appl. No. 17/654,949, mailed on May 23, 2022, 2 pages.

Notice of Allowance for U.S. Appl. No. 29/643,240, mailed on Aug. 10, 2020, 7 pages.

Notice of Allowance for U.S. Appl. No. 29/643,241, mailed on Aug. 12, 2020, 8 pages.

Notice of Allowance for U.S. Appl. No. 29/643,242, mailed on May 22, 2020, 7 pages.

Notice of Allowance for U.S. Appl. No. 29/643,244, mailed on Aug. 10, 2020, 7 pages.

Notice of Allowance for U.S. Appl. No. 29/763,698, mailed on Jun. 8, 2022, 6 pages.

Notice of Allowance for U.S. Appl. No. 29/764,234, mailed on Jul. 8, 2022, 7 pages.

Office Action for U.S Appl. No. 15/134,130, mailed on May 9, 2018, 18 pages.

Office Action for U.S. Appl. No. 16/889,210, mailed on Nov. 18, 2022, 18 pages.

Office Action for U.S. Appl. No. 17/809,509, mailed on Apr. 17, 2023, 19 pages.

Office Action for U.S. Appl. No. 29/763,144, mailed on Oct. 21, 2022, 6 pages.

Office Action for U.S. Appl. No. 29/763,698, mailed on Sep. 7, 2021, 6 pages.

Office Action for U.S. Appl. No. 29/764,234, mailed on Sep. 7, 2021, 7 pages.

Shlain A., "Common Icon Set," Apr. 26, 2015, Retrieved from the Internet: URL: https://www.iconfinder.com/iconsets/common-3 , 1 Page.

Stackexchange "Dynamic Progress Indicator," Mar. 25, 2014, Retrieved from the Internet: URL: https://ux.stackexchange.com/questions/54570/dynamic-progress-indicator , 2 pages.

Staudacher I., et al., "Fully Digital Data Processing During Cardiovascular Implantable Electronic Device Follow-Up in a High-Volume Tertiary Center," European Journal of Medical Research, Oct. 11, 2017, vol. 22, No. 1, 9 pages, DOI: 10.1186/s40001-017-0284-7.

T. Tran, H.-S. Kim and H. Cho, "A Development of Ubiquitous Biomedical Interface for Facilitating Medical Device Connectivity," 7th IEEE International Conference on Computer and Information Technology (CIT 2007), Aizu-Wakamatsu, Japan, 2007, pp. 1094-1099, doi: 10.1109/CIT.2007.58 (Year: 2007).

U.S. Appl. No. 29/643,240, filed Apr. 5, 2018, Butka et al.
U.S. Appl. No. 29/643,241, filed Apr. 5, 2018, Butka et al.
U.S. Appl. No. 29/643,242, filed Apr. 5, 2018, Butka et al.
U.S. Appl. No. 29/643,244, filed Apr. 5, 2018, Butka et al.

Jul. 31, 2023—(US) Final Office Action—U.S. Appl. No. 29/763,144, 25 Pages.

Jul. 2, 2024—(JP) Office Action—App 2023-580815, 5 Pages.

May 10, 2024—(US) Notice of Allowance—U.S. Appl. No. 29/856,161, 29 Pages.

May 29, 2024—(US) Final Office Action—U.S. Appl. No. 29/763,144, 13 Pages.

"Envelope 2 Icon" Jul. 7, 2017, posted atxxx.com, [site visited Apr. 29, 2024], https://web.archive.org/web/20170707063016/https://www.iconexperience.com/i_collection/icons/?icon=envelope2 (Year: 2017).

Taylor, Nick Paul, "Murj scoops $8.5M to enable boom in devices and data" May 9, 2018, posted at fiercebiotech.com, [site visited Apr. 29, 2024], https://www.fiercebiotech.com/medtech/murj-scoops-8-5m-to-enable-boom-devices-and-data (Year: 2018).

* cited by examiner

SYSTEMS AND METHODS TO MONITOR PATIENT DEVICES

FIELD

Aspects of the presently disclosed technology relate generally to patient device monitoring and, more particularly, to systems and methods for remotely monitoring one or more cardiac implantable electronic devices.

BACKGROUND

Implantable medical devices are regularly used to treat and/or monitor a variety of medical conditions. For example, cardiac implantable electronic devices (CIED), such as implantable cardioverter defibrillators (ICDs) are often utilized to regulate and monitor cardiac functions. CIEDs may include, without limitation: pacemakers (PMs), which prevent slow heart rates using low-energy electrical pulses; implantable cardioverter defibrillators (ICDs), which are used to detect abnormal heart arrhythmias and deliver life-saving shocks to prevent sudden cardiac arrest; implantable loop recorders (ILRs) and implantable cardiac monitors (ICMs), which continuously monitor cardiac data and transmit data to the clinic as prescribed by a clinician and at the patient's discretion; and the like. Such CIEDs store and may periodically transmit information relating to the operation of the device outside the body for analysis, programming, and/or the like. More particularly, CIEDs store and transmit information for in-office or remote monitoring by a medical provider.

However, medical providers operating clinics are often responsible for a large number of patients having a wide range of devices. The patients can have different levels of technological sophistication and often follow different care plans. These clinics are responsible for tracking the care plan activity to ensure billing requirements for monitoring periods are satisfied. However, this process is made tedious and complex by the variety of health monitoring devices available to consumers which has rapidly increased the amount of health-related data being generated. Challenges in managing devices from the clinic perspective are further compounded by the variety of different billing requirements for different care plans. The care plan for the patient can be negatively impacted and the clinic can lose revenue if the clinic fails to meet the complex array of monitoring interval requirements (e.g., by missing required data upload dates, failing to follow up, etc.).

It is with these observations in mind, among others, that various aspects of the present disclosure were conceived and developed.

SUMMARY

Implementations described and claimed herein address the foregoing problems by providing systems and methods for remote patient monitoring. In some examples, a method to manage patient devices comprises: associating a care pathway with a patient having a patient device, the care pathway defining: a particular health risk and an outcome goal value for a physiological parameter associated with the particular health risk; an outcome goal date associated with the outcome goal value; and one or more benchmark dates corresponding to one or more one or more benchmark values of the physiological parameter, the one or more benchmark dates and one or more benchmark values being based at least partly on the outcome goal value and the outcome goal date; receiving transmission data originating from the patient device; determining, from the transmission data, a measured value corresponding to the physiological parameter; determining whether the measured value is above or below a benchmark value of the one or more benchmark values; and causing an action instruction to be presented at a user device associated with the patient in response to whether the measured value is above or below the benchmark value.

In some instances, the user device is a mobile device that captures the transmission data from the patient device and transmits the transmission data to a device management platform device remote from the mobile device. Additionally, the care pathway can be defined by one or more billing codes as one or more of: a remote patient monitoring pathway; a chronic care management pathway; a primary care management pathway; a transitional care management pathway; a remote therapy monitoring pathway; or a heart failure pathway. Moreover, the physiological parameter can be one or more of: an amount of a physical activity; a heart rate; an amount of a sleep activity; a blood oxygen saturation; or an electrocardiogram (ECG) measurement. The transmission data can be first transmission data from a first device being the user device, and the method can further comprise receiving second transmission data from a second device, the second transmission data including: a measured weight value; a measured blood pressure value; a measured glucose value; or a measured temperature value. Furthermore, the second device can be: a Bluetooth device to send the second transmission data to the user device for transmission to a device management platform device; or a cellular device to send the second transmission data to the device management platform device.

In some examples, the method further includes determining that a monitoring period, associated with one or more of a first benchmark date of the one or more benchmark dates or the outcome goal date, has completed; receiving a clinician input, at a clinic user interface (UI), corresponding to the monitoring period that has completed; and generating, in response to the clinician input, a report for the monitoring period. The monitoring period can be based on one or more of a Current Procedural Terminology (CPT) billing code or a Center for Medicare and Medicaid Services (CMS) billing code. Additionally, the clinician input can be a first clinician input and the method can further comprise: receiving, at the clinic UI, a second clinician input indicating whether the monitoring period is a 30-day monitoring period or a calendar month monitoring period. The method can further comprise determining a medication consumption date associated with the patient, wherein: the transmission data is received after the medication consumption date; and the benchmark value is at least partly based on the medication consumption date.

In some examples, a method to manage a patient device comprises: associating a care pathway with a patient having a device based on a clinician input received at a clinic user interface (UI), the care pathway defining: a particular health risk associated with one or more physiological parameters; and one or more predetermined threshold values corresponding to the one or more physiological parameters; receiving transmission data originating from the patient device; determining, from the transmission data, a measured value corresponding to a physiological parameter of the one or more physiological parameters; determining whether the measured value is above or below a predetermined threshold value of the one or more predetermined threshold values; presenting an indication of whether the measured value is above the predetermined threshold value at the clinic UI;

and causing an action instruction to be presented at a patient UI displayed at a user device associated with the patient in response to whether the measured value is above or below the predetermined threshold value.

Furthermore, in some instance, the action instruction indicates an amount of steps to be walked for a number of one or more days. The clinician input can be a first clinician input, and the method can be further comprise: receiving a second clinician input at the clinic UI indicating the predetermined threshold value; storing the predetermined threshold value at a device management platform storage device in response to the second clinician input; and retrieving the predetermined threshold value from the device management platform storage device to determine whether the measured value is above or below the predetermined threshold value. Moreover, the method can further comprise receiving a third clinician input at the clinic UI in response to presenting the indication of whether the measured value is above the predetermined threshold value, causing the action instruction to be presented at the patient UI is in response to the third clinician input. Additionally, the method can comprise receiving an updated data transmission in response to causing the action instruction to be presented at the patient UI.

In some examples, a method to manage an patient device comprises: associating a plurality of care pathways with a plurality of patients having a plurality of patient devices, a care pathway of the plurality of care pathways defining: a particular health risk for a patient of the plurality of patients, the particular health risk being associated with one or more physiological parameters; and one or more predetermined threshold values corresponding to the one or more physiological parameters; receiving transmission data originating from the plurality of patient devices; receiving, at a clinic user interface (UI), a first clinician input selecting a patient identifier corresponding to the patient; determining, from the transmission data and in response to the first clinician input, a measured value corresponding to a physiological parameter of the one or more physiological parameters for the patient; presenting, at the clinic UI, an indication of whether the measured value is above or below a predetermined threshold value of the one or more predetermined threshold values; and causing an action instruction to be presented at a patient UI displayed at a user device associated with the patient in response to a second clinician input at the clinic UI.

In some examples, the action instruction is a first action instruction, and the method further comprises: determining user device parameters of the user device associated with the patient; determining that the user device parameters fail to satisfy a device requirement associated with the care pathway; and causing, in response to the user device parameters failing to satisfy the device requirement, one or more of: a second action instruction to be presented at the patient UI displayed at the user device; or a complimentary device to be shipped to a physical address associated with the patient identifier. The method can further comprise: receiving, a third clinician input at the clinic UI; and presenting, in response to the third clinician input, a patient profile including two or more of: a device type or parameter of the user device; the care pathway associated with the patient; a device requirement associated with the physiological parameter defined by the care pathway; a latest measured value associated with an outcome goal; or an indication of whether the measured value is greater than a benchmark value. Additionally, the method can comprise: determining a Current Procedural Terminology (CPT) billing code associated with the care pathway; determining a monitoring period associated with the CPT billing code, the one or more predetermined threshold values including a benchmark value for the monitoring period; determining a data transmission schedule corresponding to the monitoring period; and causing the user device to transmit the transmission data according to the data transmission schedule. Finally, the CPT billing code can be a first CPT billing code, and the method can further comprise: determining that clinician activity or a data transmission fails to satisfy a first requirement of the first CPT billing code for the monitoring period; and in response to the clinician activity or a data transmission failing to satisfy the first requirement of the first CPT billing code, determining that the clinician activity or the data transmission satisfies a second requirement of a second CPT billing code for the monitoring period; and generating a report corresponding to the second CPT billing code instead of the first CPT code for the monitoring period.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

DETAILED DESCRIPTION

Aspects of the present disclosure involve systems and methods for managing patient devices using a device management platform. The device management platform can provide multiple services to a clinic system in communication with a patient system to improve the effectiveness of procedures performed by the clinic system, resulting in improved care to the patient as well as increased revenue for the clinic.

For instance, the device management platform can determine outcome goal values and outcome goal dates, with multiple benchmarks, corresponding to measured physiological parameters of the patient. These can be particularized for the patient based on a type of health risk being monitored, a care pathway defined for the patient, and/or a monitoring interval requirement defined by a billing procedure. As such, the device management platform can aggregate and analyze transmission data received from the patient system to determine whether an amount of data transmissions (e.g., and/or a schedule of data transmissions) satisfies a billing requirement for a particular monitoring period, and to determine whether physiological parameters for the patient are improving at the rate intended by the care plan. Based on these determinations, the device management platform can cause various action instructions to be generated or presented at a patient user interface (UI) and/or a clinic UI as to intervene in the care plan.

Furthermore, the device management platform can generate a workflow interface at the clinic system (e.g., the clinic UI) based on the care pathway, a billing pathway, the outcome goal values and dates, the benchmarks, and the measured physiological parameters. The workflow interface can present this data and other data of the device management platform in an intuitive manner that can be easily navigated by clinic personnel to perform device monitoring and management tasks. For instance, the workflow interface can include a parameter monitoring interface section, a goal tracker bar, and other features to simplify the complex aggregation of these different types of data.

Accordingly, workflow processes of the clinic system for monitoring and tracking patient care can be made more efficient while reducing the likelihood of errors (e.g., missed clinic actions, missed patient actions, missed deadlines, etc.). This results in improved care for the patient and increased revenue for the clinic alike. Moreover, the device management platform can collect data related to patient outcomes to determine which clinic processes and/or patient system characteristics correlate to improved patient outcomes. Data can also be collected related to clinic actions to provide insights into clinic action trends that result in improved patient care and/or increased revenue. Additional advantages will become apparent from the disclosure herein.

Figure 1:
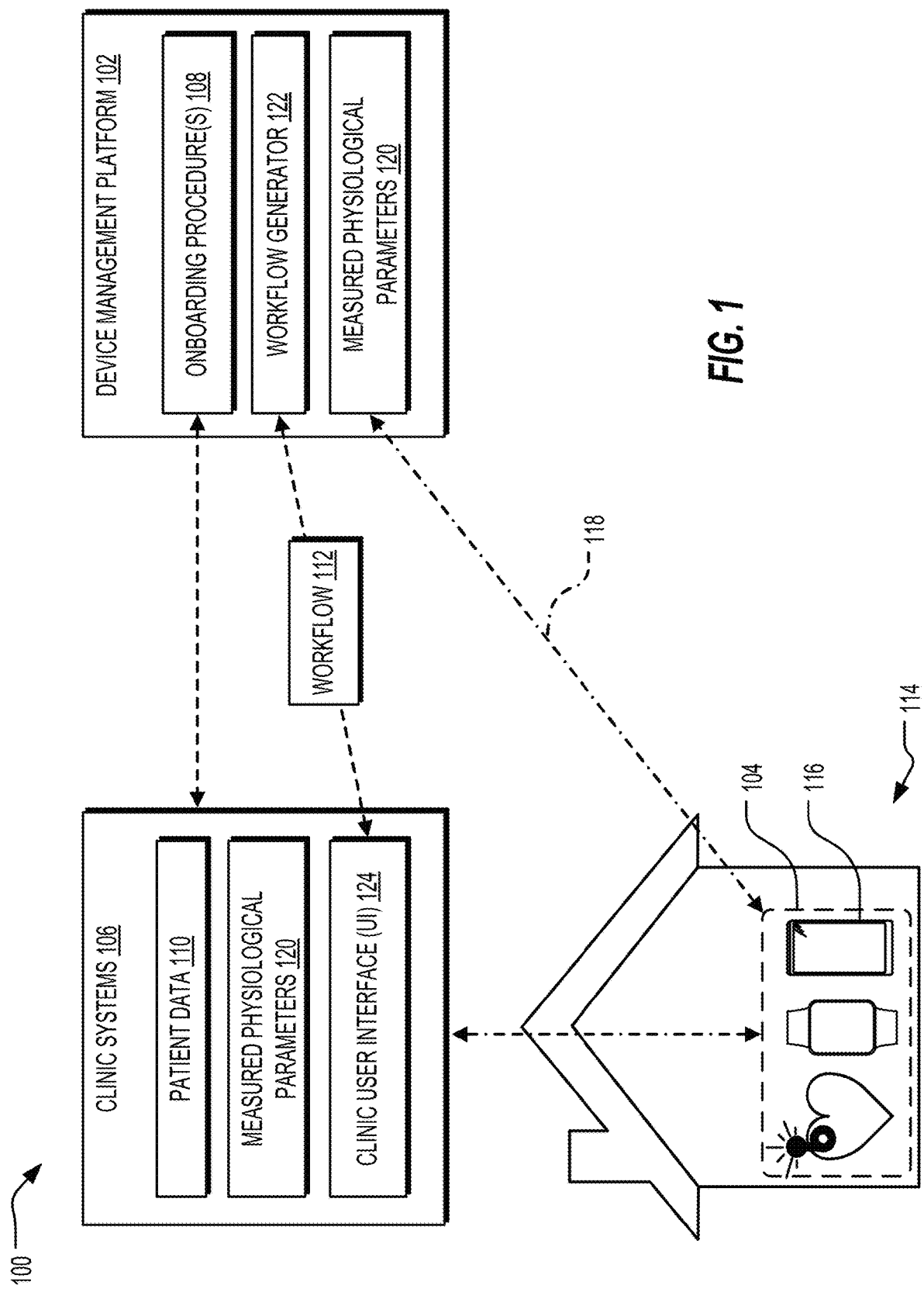
FIG. 1 illustrates an example system for managing patient devices using a device management platform.

FIG. 1 illustrates an example system 100 including a device management platform 102 for managing one or more patient devices 104 of one or more patients. The device management platform 102 can be one or more of an application, a Software-as-a-Service (SaaS) and/or a cloud-based service or remotely provided service. For instance, one or more clinic system(s) 106 can download an application from a server of the device management platform 102 and/or can interact with a web portal provided by the device management platform 102 to receive access to the device management platform 102. In some examples, the device management platform 102 provides one or more onboarding procedure(s) 108 such as a clinic onboarding process for the clinic system(s) 106 to integrate clinic data (e.g., patient data 110 such as patient records, other patient data 110, clinic personnel data, relevant billing codes, etc.) into a cardiac device management service provided by the device management platform 102. The onboarding process for the clinic system(s) 106 can also include building out various workflows 112 corresponding to the patients based on various factors, as discussed in greater detail herein.

In some examples, the system 100 includes one or more patient system(s) 114. The patient system(s) 114 can include the patient device(s) 104, which can include at least one of: a mobile device, a wearable device, a smart watch, a CIED, an ICD, a PM, an ILR, an IMC, a blood testing cuff, a blood pressure cuff, an activity tracker, a blood pressure monitor, a continuous glucose monitoring (CGM) device, a glucometer, a heart rate monitor a heart rate/blood pressure device, a peak flow meter, a pulse oximeter, a scale, a sleep tracker, a thermometer, an Internet-of-Things (IoT) device, and the like. The patient device(s) 104 can be a single device or can include multiple devices (e.g., a primary device in communication with a secondary device 116) to create and/or send transmission data 118. In one embodiment, the secondary device 116 can be a mobile device and/or wearable device of the patient which receives transmission data 118 from a CIED via a Bluetooth®, Wi-Fi, or other local area network connection.

The patient device(s) 104 can send the transmission data 118 to the device management platform 102 and/or the clinic system 106. The transmission data 118, which can originate at the patient device 104 (e.g., and/or another device, such as the secondary device 116, an Internet-of-Things, a wearable device, combinations thereof, and the like) and can include data representing measurements of one or more physiological parameters, such as a heart rate, an amount of physical activity, an amount of sleep activity or an indication of sleep deprivation, a blood oxygen saturation level, an electrocardiogram (ECG) measurement, a body temperature, a body weight, a glucose level, and the like. These measured physiological parameter(s) 120 can be captured and time-stamped in the transmission data 118 and sent to one or both of the device management platform 102 and/or the clinic system(s) 106. In some instances, measured physiological parameter(s) 120 data can be pulled from the patient system 114 periodically according to a transmission schedule and/or manually in response to a request. In some examples, different types of data may have different data pull schedules (e.g., a blood pressure data type can be pulled multiple times a day whereas a body weight data type can be pulled once a day or once a week, etc.).

Accordingly, the device management platform 102 and/or the clinic system(s) 106 can use the measured physiological parameter(s) 120 to determine whether the patient is on track to meet an outcome goal associated with a particular health risk and/or whether any workflow actions can be taken to increase a likelihood of meeting the outcome goal, ultimately improving care for the patient.

Moreover, the device management platform 102 can improve the clinic system(s) 106 by providing workflows 112 corresponding to the patients of the clinic system 106 with a workflow generator 122. The workflow generator 122 can use various inputs to generate goal outcomes associated with the patient, benchmarks calculated based on the goal outcome, care pathways, billing pathways, and other features of the device management platform 102 used to track, monitor, organize, and utilize the transmission data 118 to provide patient care, as discussed in greater detail below. By presenting the outputs of these features of the workflow generator 122 at a clinic user interface (UI) 124, the device management platform 102 can streamline many internal processes for the clinic, improving clinic efficiency while reducing clinic errors and lost billing opportunities. The device management platform 102 can present information at the clinic UI 124 incorporating patient data 110 (e.g., identification information, biological information, health information, and the like), the measured physiological parameters 120, as well as various components of the workflow 112 (e.g., goal outcomes, benchmarks, care pathways, billing pathways, etc., as discussed in greater detail below). Additionally, the device management platform 102 can generate an intuitive interface with multiple filters and analysis capabilities to keep clinic personnel up-to-date on actions needed (e.g., by the clinic personnel and/or the patient) to manage the patient device 104 and provide patient care for the cardiac device patient consistent with clinic standards, industry standards, and billing codes. Additional benefits are discussed below.

Figure 2:
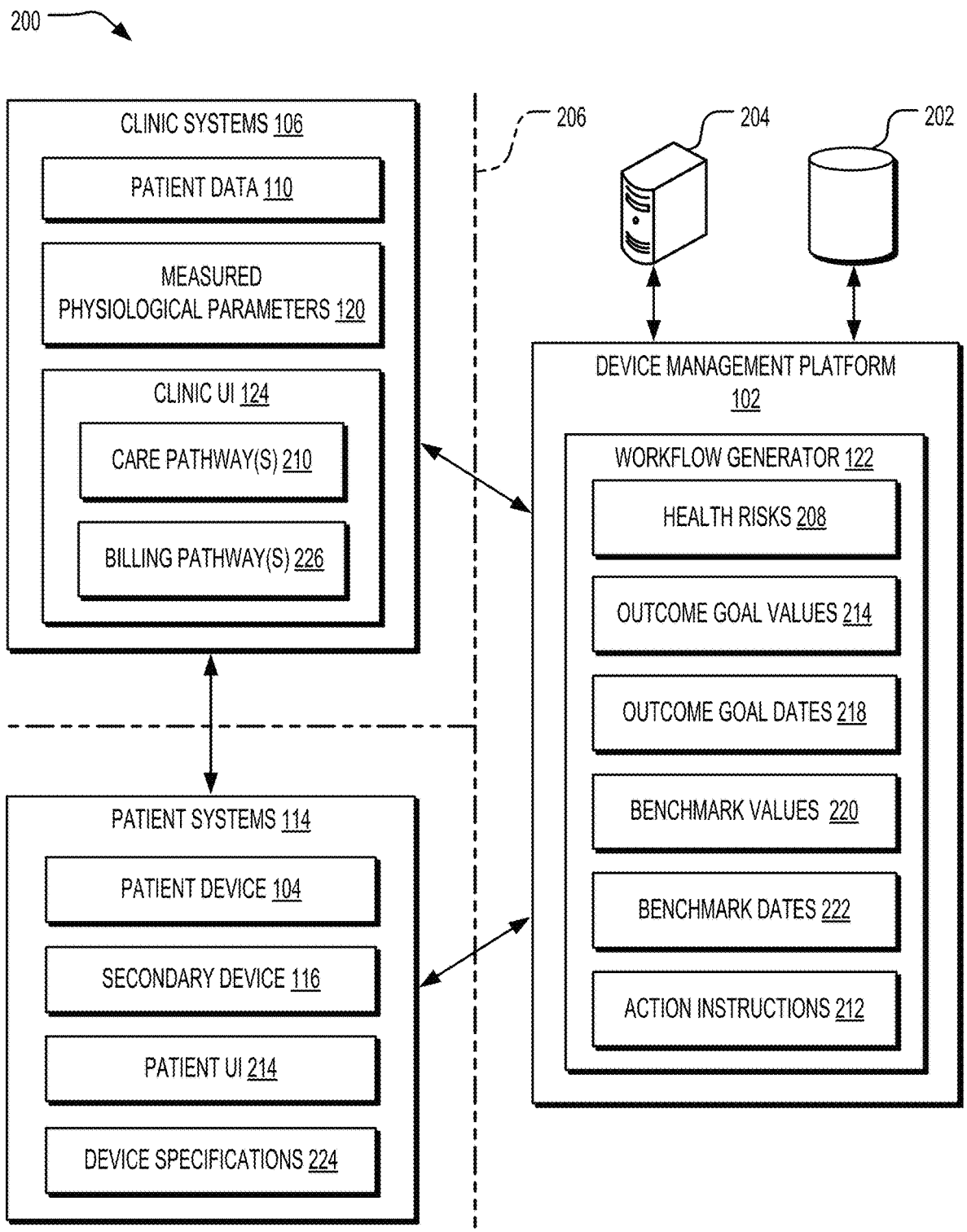
FIG. 2 illustrates an example system for managing patient devices using a device management platform with a workflow generator, which can form at least a portion of the system of FIG. 1.

Turning to FIG. 2, an example system 200 for managing the patient device(s) 104 is depicted, which can form at least a portion of the system 100 depicted in FIG. 1. The system 200 can include the device management platform 102, stored at one or more database(s) 202 and/or executed by one or more servers 204, to generate and/or present various workflow components at the clinic system 106, as discussed in greater detail below.

As noted above, the device management platform 102 can be provided as a cloud-based service, as a locally-stored application at the clinic system 106, and combinations thereof. As such, the database(s) 202 and/or the server(s) 204 of the device management platform 102 can be located remote from the clinic systems 106 but can also include hardware components at the clinic systems 106. Similarly, software components of the device management platform 102, such as the workflow 112 discussed herein, can be hosted remotely at the database(s) 202 and executed remotely by the server 204, and/or hosted and executed locally at the clinic system(s) 106. The database(s) 202 can store any of the data files and/or software instructions discussed herein, including associations between these different data files. Moreover, the data in the database(s) 202 can be aggregated and associated with clinic profiles associated with the clinic system 106, clinic site profiles corresponding to sites of the clinic system 106, and/or patient profiles associated with the patient system 114 to perform the operations discussed herein (e.g., to generate the UIs, filtering, and/or analytics services). The one or more server device(s) 204 may be a single server, a plurality of servers with each such server being a physical server or a virtual machine, or a collection of both physical servers and virtual machines. The server(s) devices 204 may represent an instance among large instances of application servers in a cloud computing environment, a data center, or other computing environment. The one or more databases 202 and/or the one or more server device(s) 204 can form at least a portion of a computing system of the device management platform 102, as discussed below regarding FIG. 12.

In some examples, the patient system(s) 114 can communicate with the device management platform 102 and/or the clinic system(s) 106 by connecting to one or more network(s) 206. The network(s) 206 can be one or more of a local area network (LAN) (e.g., Wi-Fi, Bluetooth®, Near Field Communication (NFC), etc.) a wide area network (WAN) (e.g., ethernet, fiber, Internet-of-Things (IoT), the Internet, etc.), a cellular network (e.g., third generation (3G), fourth generation (4G), Long-Term Evolution (LTE), fifth generation (5G), etc.), and the like.

In some instances, the device management platform 102 can generate the workflow 112 to include multiple workflow components, attributes, and pathways, and care plans, and can present these at the clinic system 106 via the clinic UI 124. For instance, the workflow 112 can determine one or more health risk(s) 208 (e.g., health issue indications) associated with a particular patient for which the workflow 112 is generated. The health risks 208 can include hypertension, post ablation, heart failure, chronic obstructive pulmonary disease (COPD), being overweight, being sleep deprived, and/or combinations thereof. the different health risks 208 can each correspond to a different care plan. In some instances, medical personnel can input a first health risk as a primary indication or primary health risk for the patient (e.g., hypertension, post ablation, heart failure, and/or COPD) and a second health risk as a secondary indication or a secondary health risk for the patient (e.g., being overweight or being sleep deprived.). The care plans for the primary and/or secondary health risks can be used by the device management platform 102 for various downstream processes of generating workflow attributes, care pathways 210, action instructions 212, and the like, as discussed in greater detail below.

In some examples, the device management platform 102 can generate the workflow 112 to include one or more care pathways 210. The care pathways 210 can be based on industry defined procedures corresponding to how the clinic engages with the patient, and can integrate the patient data 110, measured physiological parameter(s) 120, and various inputs from medical personnel at the clinic UI 124 into a care plan with defined benchmarks, outcomes, and data flows to implement such strategies. A single care pathway 210 can include multiple care plans and, inversely, a single care plan can include multiple care pathways 210. For a particular care pathway 210 to address a particular health risk 208 (e.g., hypertension), the workflow generator 122 can determine one or more outcome goal values 214. The outcome goal value 214 can be a value for the measured physiological parameter(s) 120 (e.g., blood pressure) corresponding to the health risk 208 of the care pathway 210 (e.g., hypertension). The one or more outcome goal values 214 can be considered a healthy value and can be an intended value to be achieved as an outcome of the workflow 112 for the care pathway 210. The outcome goal values 214 can be based on industry-recognized healthy values for the physiological parameters, such as a target average blood pressure for reducing the hypertension health risk 208, and the like. The various care pathways 210 are discussed in greater detail below regarding FIG. 5. Additionally or alternatively, the outcome goal value(s) 214 can be determined or set based on input received at the clinic UI 124 (e.g., by clinic personnel) and/or input received at a patient UI 216 of the patient system(s) 114.

In some instances, the outcome goal value(s) 214 can be associated with one or more outcome goal dates 218 (e.g., indicating an end of a monitoring period or multiple monitoring periods), by which the physiological parameter is to be at or below the one or more outcome goal values 214. The one or more outcome goal dates 218 can be based on a variety of factors, such as an initial measured value for the physiological parameter corresponding to the one or more outcome goal values 214, a difference between the initial measured value and the one or more outcome goal values 214, a selected rate of change, a selected amount of change per month, a monitoring period defined by a billing code, or combinations thereof. Furthermore, the care plan can include one or more benchmark values 220 associated with one or more benchmark dates 222. The benchmark values 220 can be based on the outcome goal values 214 and the outcome goal dates 218 and can represent incremental steps to reaching the one or more outcome goal values 214. The one or more benchmark values 220 and benchmark dates 222 can be determined by first determining the difference between the initial measured value and the outcome goal value 214, then dividing this difference by a number of monitoring periods until the outcome goal date 218. For example, the outcome goal date 218 may be one year from a starting date, and the benchmark dates 222 can be the end of each calendar month to define twelve monitoring periods until the outcome goal date 218. In some examples, the clinic UI 124 can receive an input defining whether the monitoring period is a calendar month or a 30-day period. In examples where the health risk 208 is hypertension, outcome goal values 214 can be systolic blood pressure of 120 mm Hg and diastolic blood pressure of 80 mm Hg. If the difference between the initial measured value and these outcome goals value 214 is 60 mm Hg, the benchmark values 220 can be determined by dividing the difference by the number of monitoring periods (e.g., benchmark dates 222) which, in this example, provides incremental benchmark values of 5 mm Hg per monthly monitoring period. As discussed in greater detail below, the device management platform 102 can present this care plan information at the clinic UI 124 to improve patient care. For instance, the device management platform 102 can use the one or more outcome goal values 214, the one or more outcome goal dates 218, the one or more benchmark values 220, and the benchmark dates 222 to determine when to generate and send action instructions 212.

In some examples, the patient system 114 includes the patient device 104, the secondary device 116 (e.g., mobile phone), and various other devices, such as wearable devices, IoT devices, tablets, and the like. The hardware and software components of these devices comprising the patient system(s) 114 can include various device specifications 224. For instance, the various device specifications 224 can include one or more sensors in the patient device(s) 104 and/or the secondary device 116 (e.g., a motion sensor, a temperature sensor, etc.), a connectivity capability (e.g., Wi-Fi, Bluetooth®, or cellular such as Fourth Generation (4G) or Fifth Generation (5G)), an operating system compatibility, a memory capacity, a processing power (e.g., an of random-access memory (RAM)), and the like. From the device specifications 224 (e.g., and other information, as discussed below), the device management platform 102 can determine a technology tier corresponding to the patient and, based on the technology tier, can generate one or more action instructions 212 (e.g., to procure a particular device). The device management platform 102 can also generate and/or present one or more billing pathways 226, which can integrate with the care pathways 210 to form the workflow 112 and create billing opportunities.

Figure 3:
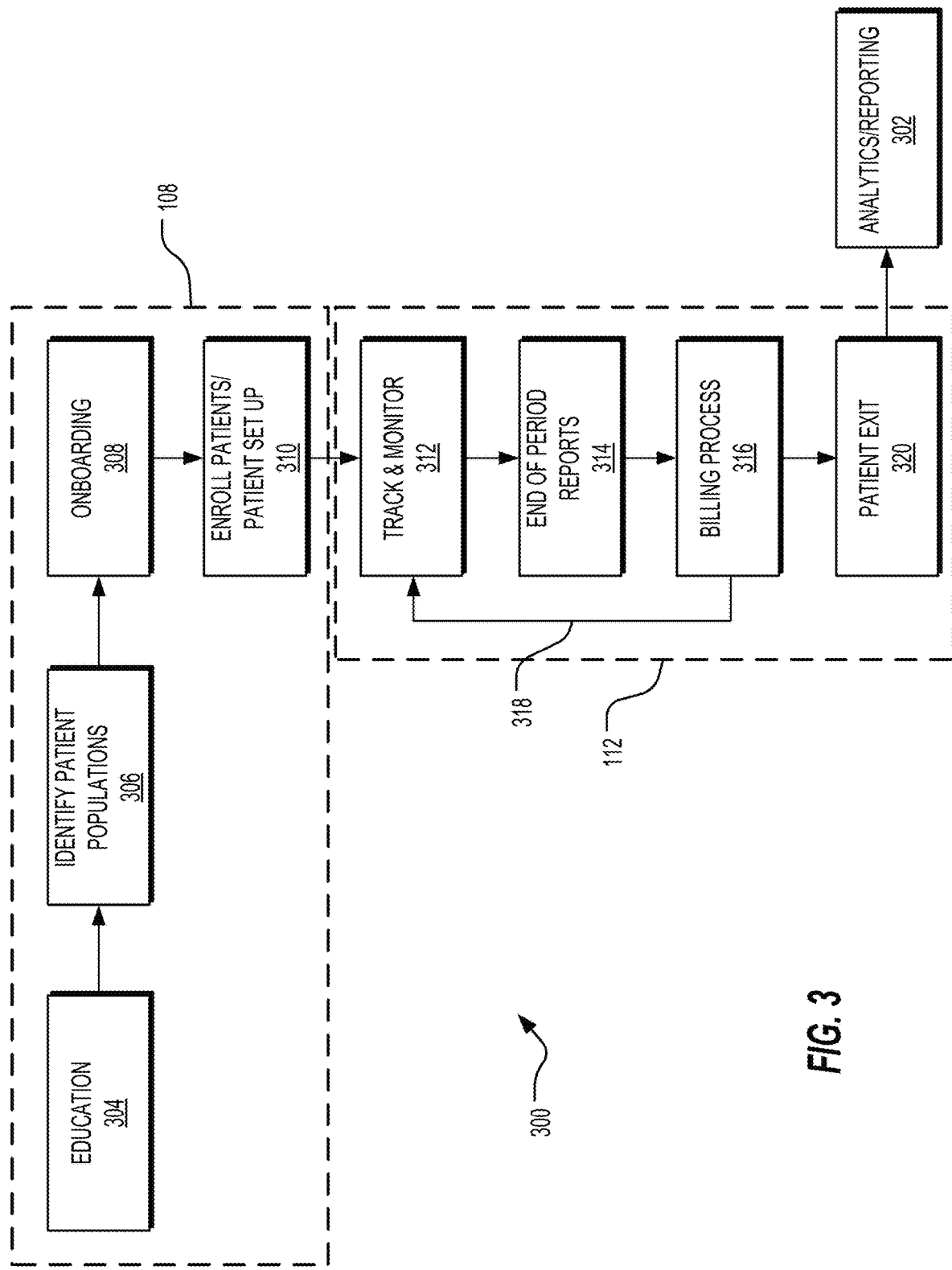
FIG. 3 illustrates an example system for managing patient devices using a data flow performed by the device management platform, which can form at least a portion of the system of FIG. 1.

FIG. 3 illustrates an example system 300 to manage the patient device(s) 104, which can form at least a portion of the system 100 of FIG. 1. FIG. 3 illustrates a data flow of the system 300 that includes the one or more onboarding procedures 108, the workflow 112, and an analytics and reporting process 302. The components of the device management platform 102 depicted in FIG. 3 are discussed in greater detail throughout this disclosure.

In some examples, the onboarding procedure 108 can include an education operation 304. At the education operation 304, the device management platform 102 can provide information to the clinic system 106 educating the clinic personnel on techniques for monitoring the patient device(s) 104, such as the various features of the device management platform 102 discussed herein. The one or more onboarding procedure(s) 108 can also include a patient population identification operation 306 in which patient populations for the clinic are identified (e.g., based on the patient data 110 that is stored at the system(s) 106). Furthermore, the one or more onboarding procedure(s) 108 can include a platform onboarding process 308, in which an application is installed at the clinic system 106 and/or web portal access to the clinic UI 124 is established, and various patient data 110 and billing codes are integrated into the device management platform 102. Following the platform onboarding process 308, the device management platform 102 can perform a patient enrollment and setup process 310 to collect additional patient data 110 and associate the patient(s) identified at the patient population identification operation 306 with one or more workflows 112. The patient enrollment and setup process 310 can include importing data from an electronic medical records (EMR) and/or manually entering the patient data 110. The patient data 110 can include personal data (e.g., the full patient name, date of birth, sex, contact information, etc.), as well as medical data when the patient gives such consent (e.g., an enrollment date, a list of medications, a diagnosis, vital signs, a medical history, a medical diagnosis, an immunization date, an allergy, one or more lab test results, and the like).

The patient data 110 can also include one or more technology tiers associated with the patient. The technology tiers can indicate a technological capability of the user based on other patient data 110 as well as other types of data, such as the various device specifications 224. The technology tiers can indicate what technology capabilities (e.g., types of sensor data) are required at the patient system 114 to provide the input data to the care pathway 210 and/or the billing pathway 226. For instance, the device management platform 102 can determine technology requirements for the care pathway 210 and/or the billing pathway 226, such as a Wi-Fi requirement, a cellular signal requirement, a blood test requirement, and/or a smart phone requirement. The technology tier can include information of an additional contact person for the patient, including their technology capabilities and contact information. Some of the technology capabilities and devices of the patient that can be indicated by their technology tier can be a type of smart watch, a blood testing cuff, a blood pressure cuff, an activity tracker, a blood pressure monitor, a continuous glucose monitoring (CGM) device, a glucometer, a heart rate monitor a heart rate/blood pressure device, a peak flow meter, a pulse oximeter, a scale, a sleep tracker, a thermometer, and the like. By defining various technology tiers for the patient, the device management platform 102 can determine whether the patient is using or has access to any of these devices, and whether any of these devices are needed by the data requirements of the care pathways 210 and/or the billing pathway 226. Accordingly, if it is determined that the technology tier requires a device capability that is lacking, the device management platform 102 can send an action instruction 212 to the patient system 114 to procure these devices and/or an instruction to cause any of these devices to be delivered to a location associated with the patient system 114.

In some instances, the device management platform 102 can generate the workflow 112 following the one or more onboarding procedure(s) 108 to monitor and manage the patient device 104 of the patient enrolled during the patient enrollment and setup process 310. The workflow 112 can include a tracking and monitoring process 312 performed during the monitoring period and/or multiple monitoring periods and an end of period reporting process 314 for generating a report corresponding to the monitoring period (e.g., in response to the outcome goal date 218 occurring or the benchmark date 222 occurring). The tracking and monitoring process 312 is discussed in greater detail below. In some examples, the workflow 112 can include a billing process 316, which can be defined by the one or more billing pathways 226 integrated into the workflow 112 and/or the care pathway 210. In some instances, the device management platform 102 can perform one or more billing period iterations 318 in which the tracking and monitoring process 312, the reporting process 314 and the billing process 316 are repeated for a series of sequential monitoring periods (e.g., corresponding to the benchmark dates 222). The workflow 112 can include a patient exiting step 320 to occur once the outcome goal value 214 is reached, the outcome goal date 218 occurs, and/or another action occurs to end the workflow 112 with respect to the patient and a particular care plan. Once the workflow 112 for the patient is complete (e.g., and/or concurrently with the workflow 112), the device management platform 102 can perform the analytics and reporting process 302. The analytics and reporting process 302 can generate analytics corresponding to the patient enrolled at the patient enrollment and setup process 310, the plurality of patients identified at the patient population identification operation 306, the clinic itself, a particular site or a plurality of sites of the clinic, and/or a plurality of clinics, as discussed in greater below regarding FIG. 11.

Figure 4:
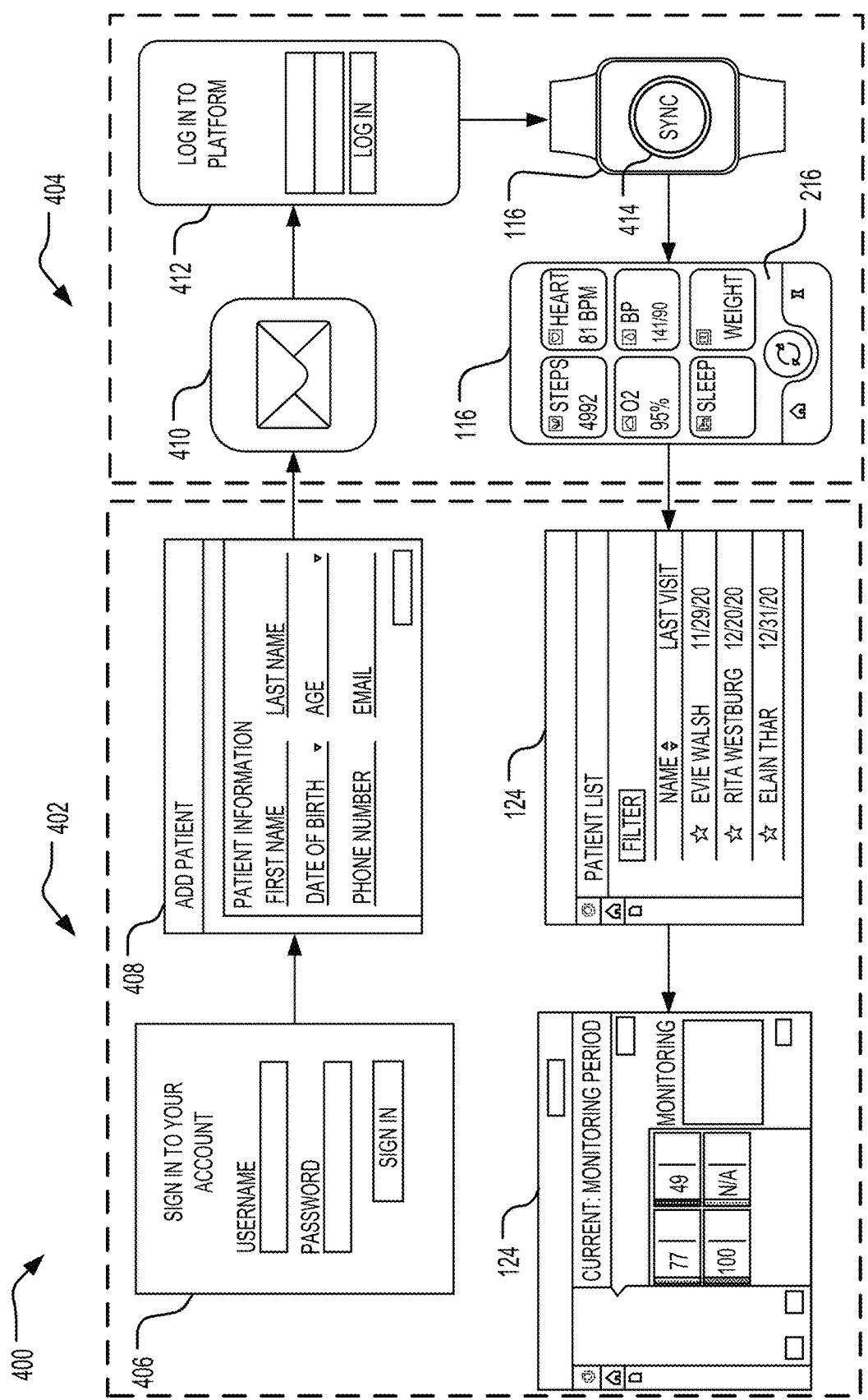
FIG. 4 illustrates an example system for managing patient devices including a patient enrollment and setup process, which can form at least a portion of the system of FIG. 1.

FIG. 4 illustrates an example system 400 to manage the patient device(s) 104, which can form at least a portion of the system 100 of FIG. 1. The system 400 depicted in FIG. 4 can include at least the patient enrollment and setup process 310 which can use communications between the patient system 114 and the clinic system 106 to bring the patient data 110 into the device management platform 102 and initiate the workflow 112.

In some examples, the patient enrollment and setup process 310 can include one or more messages sent between the clinic system 106 (e.g., a clinic web application 402 executing at the clinic system 106) and the patient system 114 (e.g., a mobile device or user device application 404 executing at the secondary device 116) via the network 206. The patient enrollment and setup process 310 (e.g., and any of the clinic system 106 processes discussed herein) can begin by generating and presenting a clinic login prompt 406 at the clinic UI 124 to receive clinic credentials and provide access to the device management platform 102. A create patient prompt 408 can be created and presented (e.g., in response to a clinician user input) to receive patient data 110 such as a first name, a last name, a date of birth, a sex, a gender, a phone number, and/or an email). In response to a clinician user input submitting a create patient request, a message 410 (e.g., an email, a text message, etc.) can be generated and sent to the patient system 114, for instance, presented at the patient UI 216 generated by the user device application 404. A patient login prompt 412 and/or a device sync option 414 can be presented at the patient UI 216 at the secondary device 116 (e.g. a mobile device, a wearable device, a smart watch, smart glasses, etc.) to cause the secondary device 116 to establish a communication session with the patient device 104 and/or to cause the device(s) 104 to send transmission data 118 (e.g., including the measured physiological parameter(s) 120) to the secondary device 116. A patient input selecting the device sync option 414 can also establish one or more transmission schedules or extra transmissions, for instance, as part of an initial patient onboarding process and/or in response to an action instruction 212 (e.g., generated according to the care pathways 210). The patient UI 216 can also present health metrics and one or more patient reports via the user device application 404, which can include most recent measured physiological parameter(s) 120 and/or historical measured physiological parameter(s) 120 (e.g., corresponding to activity, heart rate, an ECG, an oxygen saturation reading, an amount of sleep, a blood pressure, etc.). A patient input at the patient UI 216 can cause the patient device(s) 104 and/or the secondary device 116 to update the clinic system 106 with the latest transmission data 118 of measured physiological parameter(s) 120. In response, the clinic system 106 can receive the transmission data 118 and present, at the clinic UI 124, data related to the care plan including the measured physiological parameter(s) 120 with the patient data 110 and/or an indication of how the measured physiological parameter(s) 120 compares to the one or more outcome goal values 214 and/or the one or more benchmark values 220 (e.g., as a line graph with these threshold values shown presented as horizontal lines). The clinic web application 402 can also present the billing pathway 226 indicating how the transmission data 118 relates to the monitoring period for billing purposes (e.g., whether the transmission data 118 satisfies a monitoring interval requirement), as discussed in greater detail below.

Figure 5:
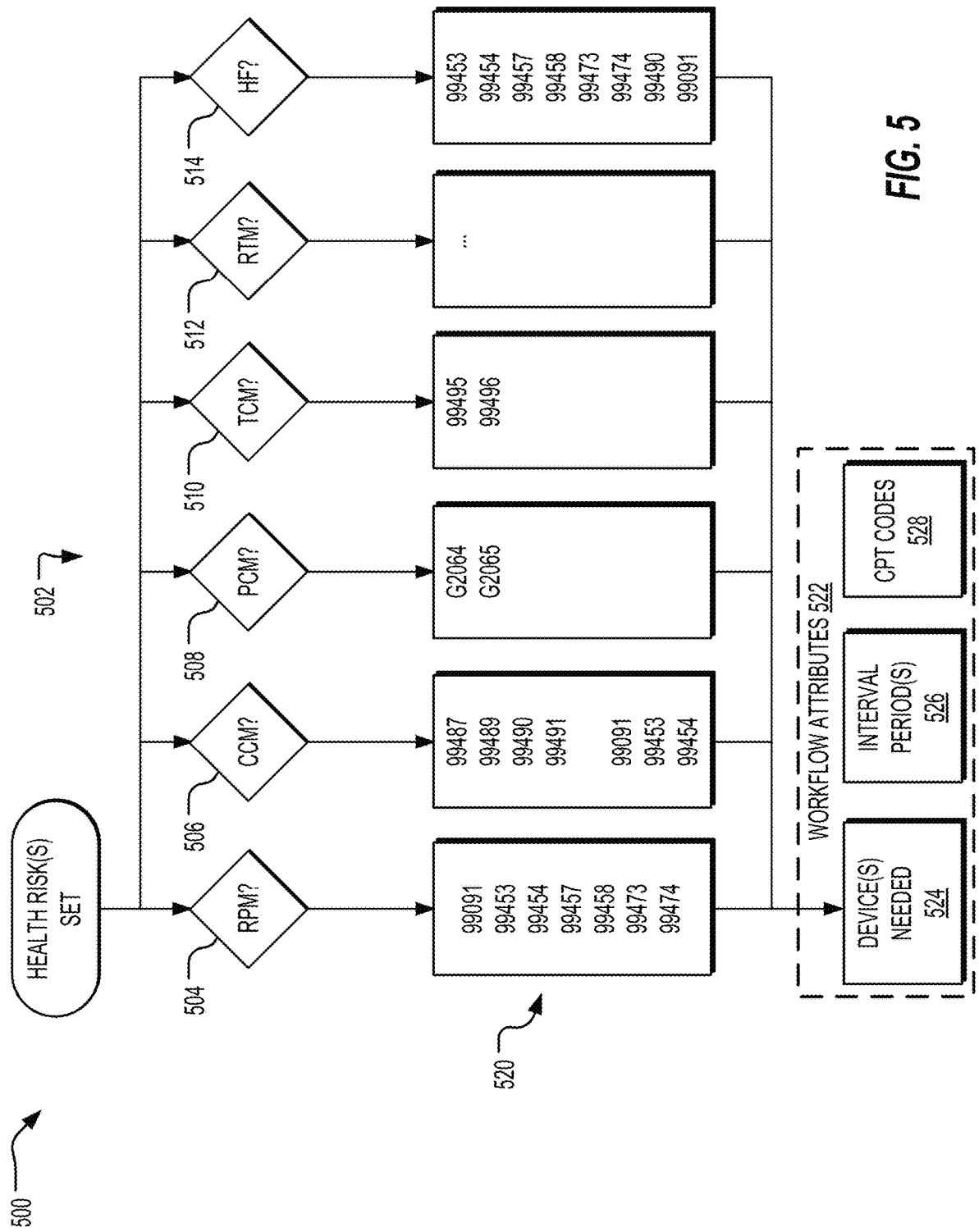
FIG. 5 illustrates an example system for managing patient devices including a billing pathway creation process, which can form at least a portion of the system of FIG. 1.

FIG. 5 illustrates an example system 500 to manage the patient device(s) 104, which can form at least a portion of the system 100 of FIG. 1. The system 500 depicted in FIG. 5 can include a billing pathway creation process 502 for determining the billing pathways 226 for the care plan generated for the patient.

In some examples, the billing pathway creation process 502 occurs subsequently to and/or concurrently with determining the health risks 208 and corresponding care plans. The billing pathways 226 can be used to construct the care pathways 210 and, additionally or alternatively, billing pathways 226 can be selected based on the care pathways 210. At the clinic system 106, an input can select one or more billing pathways 226, such as a remote patient monitoring pathway 504, a chronic care management pathway 506, a primary care management pathway 508, a transitional care management pathway 510, a remote therapy monitoring pathway 512, a heart failure pathway 518, and/or any combination of the billing pathways 226. The different billing pathways 226 can correspond to one or more billing codes 520 that define billing requirements for the particular billing pathways 226.

For instance, upon determining the billing pathway 226 for the patient (e.g., via a clinician input at the clinic system 106), and the corresponding one or more billing codes 520, the workflow generator 122 can generate various workflow attributes 522 for the workflow 112 corresponding to the billing pathway 226. The billing pathway 226 can indicate a particular type of data transmission and/or transmission schedule needed to fulfill the billing requirements (e.g., for insurance purposes) and whether the current devices of the patient can perform these functions, or whether a supplemental device request should be generated (e.g., device(s) needed 524), as discussed below regarding FIG. 6.

Moreover, the various workflow attributes 522 generated in response to the billing pathway 226 can include one or more interval periods 526 (e.g., the monitoring periods such as those defined by the outcome goal date 218, the benchmark dates 222, one or more intermediary interval periods, and the like). Additionally, the workflow attributes 522 can include one or more Current Procedural Terminology (CPT) codes 528 (+ICD-10 codes?). In some examples, a primary billing pathway can be determined corresponding to first CPT codes, and a secondary billing pathway or fall back billing pathway can be determined corresponding to second CPT codes. In some scenarios, clinic actions during the workflow 112 can fail to satisfy one or more requirements of the primary billing pathway, but can still satisfy the requirements of the secondary billing pathway. As such, the device management platform 102 can use the second CPT codes corresponding to the secondary billing pathway instead of the first CPT codes corresponding to the primary billing pathway. This technique can result in an improved workflow 112 with a higher amount of billing and billing efficiency relative to previous techniques.

Figure 6:
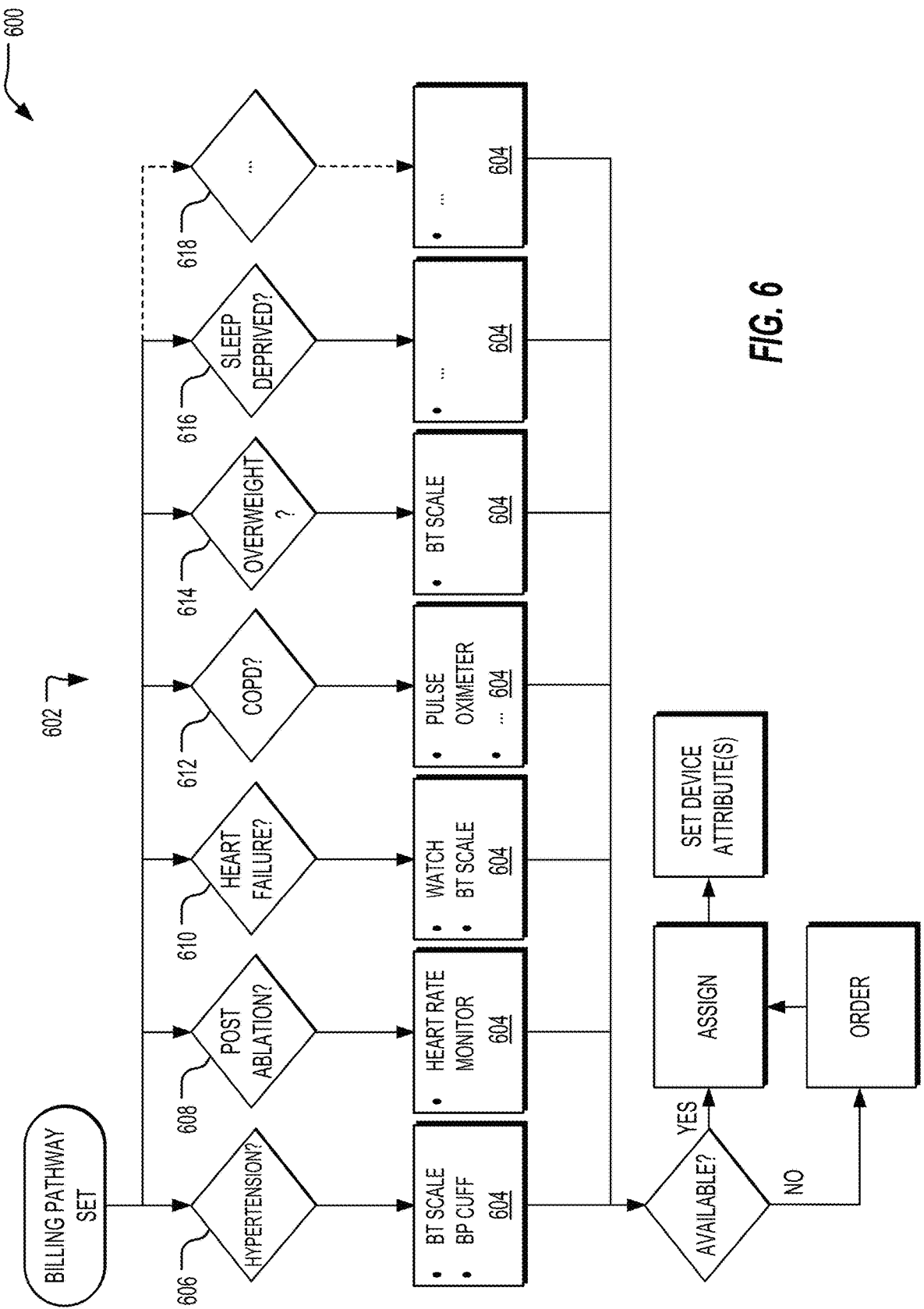
FIG. 6 illustrates an example system for managing patient devices including a device management and/or dispatching procedure, which can form at least a portion of the system of FIG. 1.

FIG. 6 illustrates an example system 600 to manage the patient device(s) 104, which can form at least a portion of the system 100 of FIG. 1. The system 600 depicted in FIG. 6 can perform a device management and/or dispatching procedure 602 to generate and/or fulfill the supplemental device request discussed above.

For instance, the device management and/or dispatching procedure 602 can include receiving the billing pathway 226 established for a patient. The device management platform 102 can assess the data requirements of the care plan to determine device capability requirements 604 corresponding to the care pathway 210. For instance, a care pathway 210 can include a hypertension care plan 606 established for the patient, and the device management platform 102 can determine that the hypertension care plan 606 has the device capability requirements 604 of a Bluetooth® scale and a blood pressure device or cuff. A post ablation care plan 608 can be established with a heart rate monitor as the device capability requirements 604. A heart failure care plan 610 can be established with a smart watch (e.g., an apple watch) and the Bluetooth® scale as the device capability requirements 604. A COPD care plan 612 can be established with a pulse oximeter as the device capability requirement 604. An overweight care plan 614 can have a Bluetooth® scale as the device capability requirement 604. A sleep deprived care plan 616 can have a Bluetooth® scale as the device capability requirement 604. Moreover, other additional or customizable care plans 618 corresponding to a customizable health risk 208 can be added and/or customizable device capability requirements 604 can be added for the customizable care plan 618 (e.g., via input(s) at the clinic UI 124).

After determining the one or more billing pathways 226, care pathways 210, care plans, and corresponding device capability requirements 604, the device management platform 102 can compare these device capability requirements 604 to device capabilities of the patient, for instance, using the technology tier data discussed above. If the device management platform 102 determines that the technology tier of the patient does not fulfill the device capability requirements 604, the device management platform 102 can order a supplemental device which does satisfy the device capability requirements 604 (e.g., via an order request API call to third-party e-commerce system or a device retailer system). If it is determined from the comparison of the device capability requirements 604 to the technology tier capabilities of the patient that the device capability requirements 604 can be provided by the patient devices (e.g., one or more secondary devices 116 already used by the patient), the device management platform 102 can assign the secondary device(s) 116 to the care pathway 210 to satisfy the device capability requirements 604. In addition to ordering and/or assigning supplemental devices to provide the device capability requirements 604 for the care pathways 210, the device management platform 102 can set one or more device attributes of the supplemental device. For instance, the device management platform 102 can generate and/or send one or more API calls to application(s) operating on the supplemental device(s) (e.g., the secondary device 116) to initiate a data collection and/or transmission process for the applications (e.g., a health application, an exercise application, a heart monitoring application, an oxygen saturation application, a body motion detection application, a location tracking application, and the like). Primary and/or secondary supplemental device(s) collecting data (e.g., sensor data) to transmit via the transmission data 118 can include one or more of the smart watch (e.g., the apple watch), the Bluetooth® scale, the blood pressure cuff, an activity tracker, a continuous glucose monitor (CGM), a glucometer, a heart rate and/or blood pressure monitor, a peak flow meter, a pulse oximeter, a scale (e.g., a network-connected scale), a sleep tracker, a thermometer, and combinations thereof.

Figure 7:
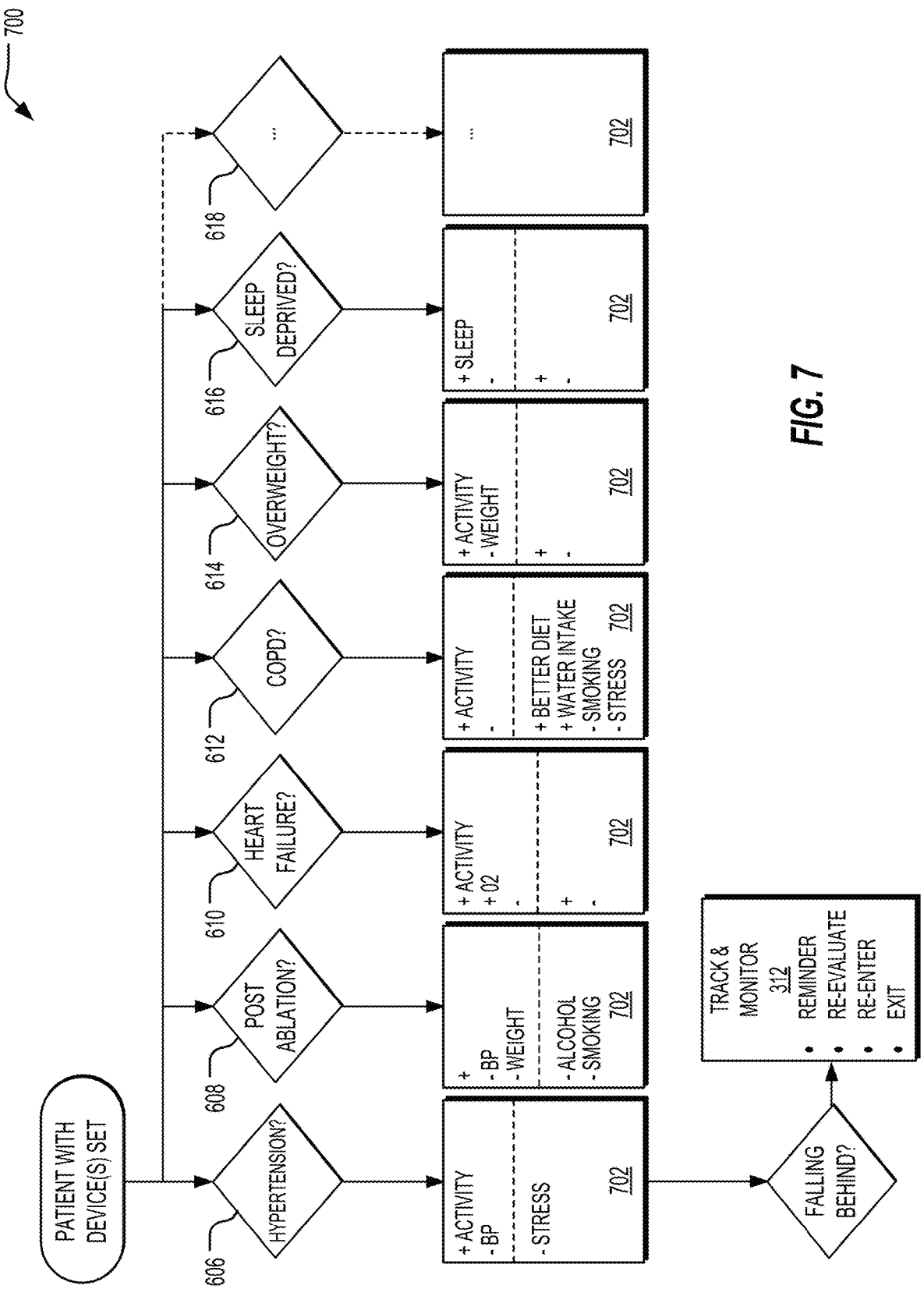
FIG. 7 illustrates an example system for managing patient devices using a care pathway and a billing pathway, which can form at least a portion of the system of FIG. 1.

FIG. 7 illustrates an example system 700 to manage the patient device(s) 104, which can form at least a portion of the system 100 of FIG. 1. The system 700 depicted in FIG. 7 can generate and present a workflow 112 that implements the billing pathway 226 and the care pathways 210 (e.g., with corresponding care plans) to generate patient outcomes corresponding to the one or more outcome goal values 214.

In some examples, the workflow 112 can have defined health goals 702 for the different care plans that correspond to the one or more outcome goal values 214 relative to a base line value. For instance, the hypertension care plan 606 can have one or more health goals 702 such as increased activity, reduced blood pressure, and reduced stress. These health goals 702 can correspond to the one or more outcome goal values 214, such a particular amount of steps or movement, a particular blood pressure value (e.g., systolic 120 mm Hg and diastolic 80 mm Hg), and/or other measured physiological parameter(s) 120 that relate to the health goals 702 of increased activity, reduced blood pressure, and/or reduced stress. The post ablation care plan 608 can have health goals 702 of reduced blood pressure, reduced body weight, reduced alcohol consumption, and/or reduced smoking relative to baseline values. The heart failure care plan 610 can have the health goals 702 of increased physical activity and increased oxygen intake relative to baseline values. The COPD care plan 612 can have the health goals 702 of increased physical activity, improved diet, increased water intake, decreased smoking, and decreased stress relative to baseline values. The overweight care plan 614 can have the health goals 702 of increased physical activity and decreased body weight relative to baseline values. The sleep deprived care plan 616 can include the health goal 702 of an increased amount of sleep relative to the baseline value.

Upon defining the health goals 702, the device management platform 102 can determine the one or more outcome goal values 214 and the outcome goal date 218, for instance, as prescribed physical data points generated by the clinic personnel (e.g., at the clinic UI 124). This can include adding one or more benchmark values 220 and benchmark dates 222 and/or interventions (e.g., action instructions 212) to the care plan, such as losing an amount of weight per week, walking an amount of steps by a particular date, taking an amount of beta-blockers each day, reaching a particular resting heart rate by a particular date, eliminating a particular diet item (e.g., red meat) for a number of months and/or increasing a particular diet item (e.g., leafy greens), reducing an amount of cigarettes smoked per day, taking a particular physiological measurement every day, and the like. One or more rationales for how the benchmark values and benchmark dates 222 relate to the goals can be added by the clinic personnel (e.g., indicating that a particular weight corresponds to a reduced blood pressure). Moreover, as discussed, above, these benchmark values 220 and/or outcome goal values 214 can be set as threshold values (e.g., by the clinic system 106) corresponding to the outcome goal date 218 and the benchmark dates 222. Additionally, the duration of the care plan can be set by the outcome goal date 218.

As discussed above regarding FIG. 6, the system 700 can perform a device management and dispatching procedure 602 to determine if a particular device is needed to satisfy the device capability requirements 604. Once the device management platform 102 completes the device management and dispatching procedure 602 or otherwise determines that the device capability requirements 604 is satisfied, the device management platform 102 can perform the tracking and monitoring process 312. The tracking and monitoring process 312 can include receiving the measured physiological parameter(s) 120 and comparing this data against the one or more benchmark values 220 and/or the one or more outcome goal values 214 to generate progress or status indicators. For instance, during the tracking and monitoring process 312, the device management platform 102 can perform a goal value comparison or benchmark value comparison to determine whether the measured physiological parameter(s) 120 are above or below the one or more benchmark values 220 and the one or more outcome goal values 214. Additionally, the tracking and monitoring process 312 can include collecting other information related to the patient, such as a report of symptoms (e.g., new symptoms). During the tracking and monitoring process 312, the device management platform 102 can determine whether the data requirements for the care pathways 210 and the billing pathway 226 are satisfied and, if not, send one or more reminders or requests to the patient system 114 to send an updated data transmission.

The device management platform 102 can also detect any status changes related to the patient during the tracking and monitoring process 312. For instance, the device management platform 102 can determine a type a medication, a date of medication consumption, and that the measured physiological parameter(s) 120 should be at particular value or within a particular range based on the medication and date of medication consumption. In other words, additional thresholds or benchmark values 220 can be determined or adjusted to measure an effectiveness of the medication consumption. Additionally or alternatively, the device management platform 102 can detect a number of office visits occurring during a monitoring period, which can be used to fulfill requirements of the billing pathway 226 and/or the care pathways 210. Moreover, one or more messages can be sent to the patient system 114 and/or the clinic system 106 to provide communications indicating statuses and progress of the care plan. The messages can be customizable (e.g., created by clinic personnel) and can include indications of the care plan progress or status, the action instructions 212, reminders, encouragement, or other information the clinic system 106 would like to transmit to the patient system 114 pursuant to causing the measured physiological parameter(s) 120 to reach the one or more benchmark values 220 and/or the one or more outcome goal values 214.

Once a monitoring period is completed (e.g., 30 days has elapsed or a month has ended), the tracking and monitoring process 312 can determine if additional evidence is needed (e.g., additional data transmissions to fill data gaps, additional patient data 110 to inform the care pathways 210 or billing pathway 226, or the like), and send a request to the patient system 114 for the additional information. Subsequently and/or concurrently with the tracking and monitoring process 312, the device management platform 102 can perform a billing process, which can aggregate the clinic actions and patient actions detected during the tracking and monitoring process 312 (e.g., during the monitoring interval), compare those actions with particular billing code requirements of particular billing codes, and generate billing report(s) which can be completed and submitted to a billing authority (e.g., an insurance provider). In some instances, the billing process can determine that a billing report is incomplete because one or more requirements of a billing code are not satisfied (e.g., a threshold number of in-office visits during monitoring period, a threshold number of transmissions during the monitoring period, etc.). In response, the device management platform 102 can determine another billing code that does have its requirements satisfied by the current status, and generate a second billing report corresponding to the other, satisfied billing code. Additionally, the device management platform 102 can send action instructions 212 to the patient system 114 requesting an action (e.g., a data transmission) to satisfy the unsatisfied billing requirement. In some examples, the device management platform 102 can determine that the one or more outcome goal values 214 have been reached by the measured physiological parameter(s) 120 falling within a predetermined range, and can send an indication to the clinic system 106 and/or the patient system 114 indicating that the outcome goal value 214 was reached and/or that the care plan is complete.

Upon onboarding the patient and the generating the workflow 112 for the patient to include billing pathway(s) 226, the care pathway(s) 210, and the various care plans, a significant amount of patient details are generated and determined. The patient details can be aggregated and/or stored with an association to a patient identifier of the patient (e.g., as a patient profile). The patient details can include the initial patient data 110 as well as a variety of data generated by the device management platform 102 related to the patient. For instance, the patient details can include general patient information (e.g., name, status with respect to the health risks 208, a medical record number (MRN), a unique management platform identifier, contact information, and/or messaging settings), technology tier information (e.g., device models and types, device capabilities, device sensors, device versions, software applications, software application versions, level of experience with technology, etc.), care team names and roles associated with the patient (e.g., a clinic personnel such as a physician, a nurse, a receptionist, etc.), and or health-related records (e.g., a list of medications, an insurance provider name, etc.). The patient details can also include data generated throughout the workflow 112, such as during the one or more onboarding procedure(s) 108 and/or the tracking and monitoring process 312. For instance, the patient details can include the primary health risk 208, the secondary health risk 208, and/or any co-morbidities associated with the patient. Moreover, the patient details can include goal progress data, such as a status of the measured physiological parameter(s) 120 and how the measured physiological parameter(s) 120 compare to the one or more outcome goal values 214 and/or the one or more benchmark values 220. The patient details can also keep a record of the action instructions 212 sent to the patient system 114 as well as actions taken in response to the action instructions 212.

Furthermore, the patient details can include the various data inputs to the device management platform 102 related to the patient, such as the measured physiological parameter(s) 120 and the various threshold values (e.g., the one or more outcome goal values 214 and the one or more benchmark values 220). Moreover, the patient details can include a histography or timeline based on (e.g., and/or indicating) the one or more outcome goal values 214, the outcome goal date 218, the one or more benchmark values 220, the benchmark dates 222, a medication prescription or change, the date of medication consumption, a data transmission record, and/or an indication of a change to the technology tier (e.g., a device change or a device addition). Moreover, the patient details can include a record of communication history for the patient, such as audio logs, communications to the patient system 114 from the clinic system 106 (e.g., the action instructions 212), communications to the clinic system 106 from the patient system 114, voicemails, internal clinic communications, and/or external clinic communications to other systems (e.g., cardiac device manufacturer systems, device ordering systems, etc.) and the like.

In some examples, the clinic system 106 can perform a report generating process to create one or more reports to be sent and/or presented at the clinic UI 124 or the patient UI 216. The report generating process can generate a report in response to many of the operations discussed herein, such as a monitoring period ending, the benchmark date 222 occurring, the outcome goal date 218 occurring, the measured physiological parameter(s) 120 satisfying the one or more outcome goal values 214 or the one or more benchmark values 220, and/or receiving an input at the clinic UI 124 requesting to generate the report. The report(s) can include any combination of the patient details discussed above, such as the histography and timeline, or other analysis results generated by the device management platform 102. The report(s) can include a primary report corresponding to the health risks 208 and/or selected care plans for the health risks 208, and one or more secondary reports, for instance, corresponding to a secondary health risk 208. Additionally, the reports can indicate a mental health, a nutrition, a breakfast, a mood, or other external factor affecting patient health. Accordingly, the report(s) can encapsulate any or all data generated during a monitoring period (e.g., for a 30-day reporting window). Furthermore, the report(s) can include additional information or side notes (e.g., generated by a physician or other clinic personnel at the clinic system 106) as well as a link to one or more past reports.

Turning to FIGS. 8-11, various examples of the clinic system 106 and the patient UI 216 are depicted. The examples of the clinic system 106 and the patient UI 216 depicted in FIGS. 8-11 can form at least a portion of the system 100.

Figure 8:
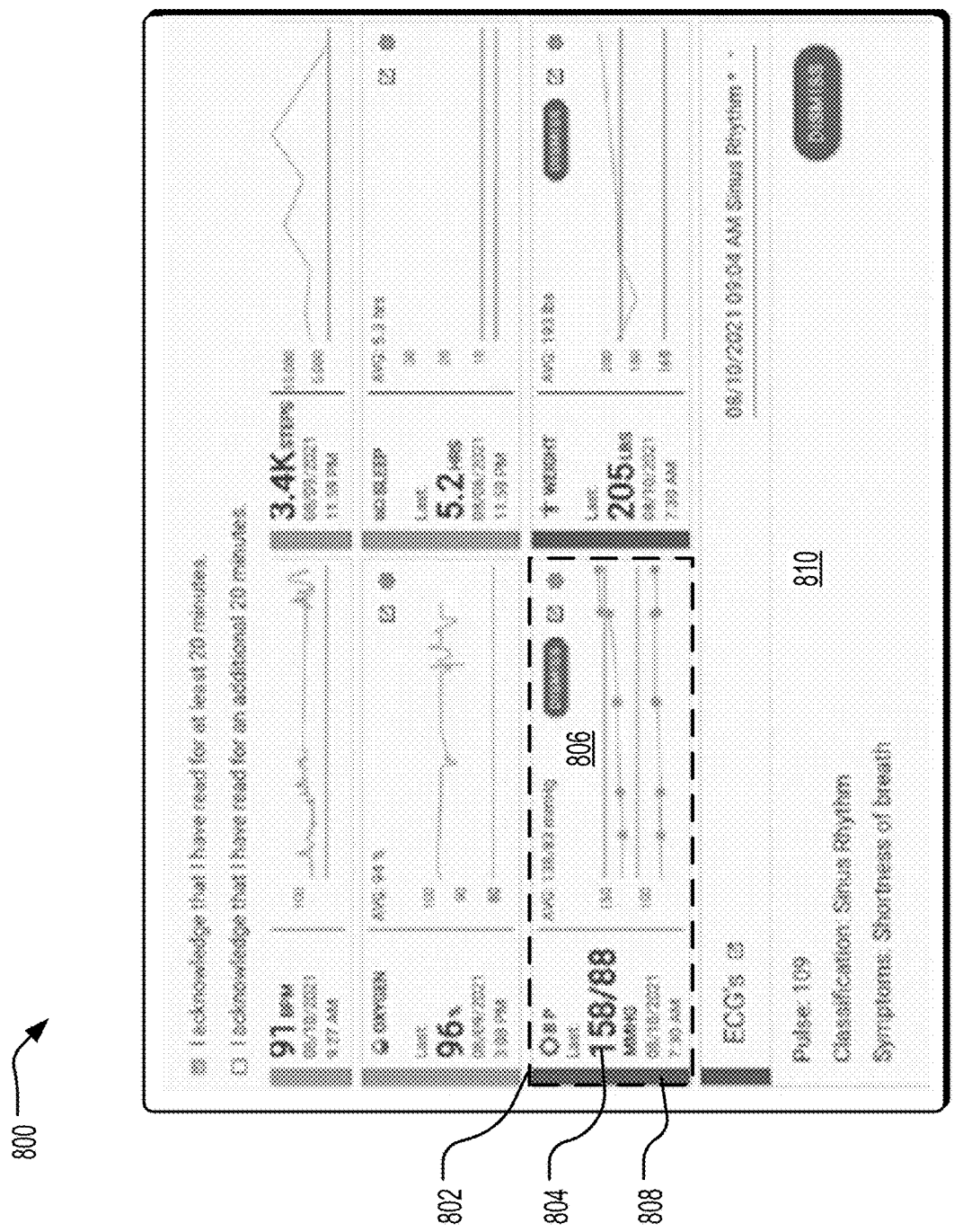
FIG. 8 illustrates an example system for managing patient devices using a parameter monitoring interface section of a clinic user interface, which can form at least a portion of the system of FIG. 1.

For instance, FIG. 8 depicts a parameter monitoring interface section 800 which can form at least a part of the clinic UI 124. The parameter monitoring interface section 800 can include one or more physical parameter sections 802 presenting the data collected and generated by the device management platform 102, for instance, during the tracking and monitoring process 312. The physical parameter section(s) 802 can correspond to the different physiological parameters being measured (e.g., heart rate, oxygen level, steps, sleep, blood pressure, weight, etc.) and can include a current or latest value 804 as well as a parameter graph 806 showing a plurality of measured physiological parameter(s) 120 graphed over time. The parameter graph 806 can also present the benchmark values 220, for instance, as one or more horizontal lines presented on the parameter graph 806. In addition to the visual representation of the parameter graph 806 showing how the measured physiological parameter(s) 120 compares to the one or more benchmark values 220, a parameter status indicator 808 can also provide a clear visual indicator of whether the measured physiological parameter(s) 120 is above or below the one or more benchmark values 220 and/or the one or more outcome goal values 214, for instance with a color coding indication (e.g., with green representing being within the benchmark range and red representing being outside the benchmark range). The monitoring interface section 800 can also present interactive interface components to receive a clinician input, such as a dismiss button for indicating acknowledgment that the measured physiological parameter(s) 120 is outside the benchmark range (e.g., above or below the one or more benchmark values 220). Additionally, the monitoring interface section 800 (and/or other portions of the clinic UI 124 can include interactive interface components to receive an acknowledgment input indicating that the clinic personnel has performed a clinic task, such as reviewing the transmission data 118 presented at the clinic UI for a particular amount of time, which can be predetermined based on one or more billing code requirements (e.g., reviewing the information for 20 minutes, reviewing the information for an additional 20 minutes, and the like). In some examples, the monitoring interface section 800 can receive an input to toggle between presenting different measured physiological parameter(s) 120.

In some examples, the monitoring interface section 800 can include an ECG section 810, which can provide information about a latest ECG transmission, including a received and/or measured time stamp, a pulse reading, a heart rhythm classification (e.g., sinus rhythm) and/or an indication of one or more symptoms.

Figure 9:
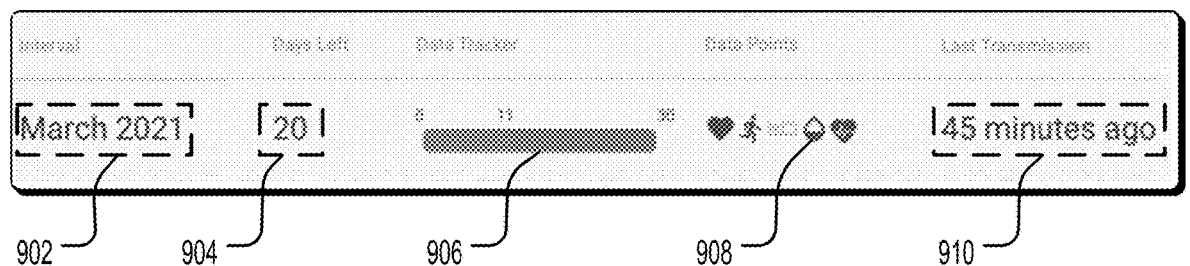
FIG. 9 illustrates an example system for managing patient devices using a goal tracker bar of a clinic user interface, which can form at least a portion of the system of FIG. 1.

FIG. 9 depicts a goal tracker bar 900 which can form at least a part of the clinic UI 124. The goal tracker bar 900 can be an elongated rectangle or banner-style portion of the clinic UI 124 and can present information related to how the measured physiological parameter(s) 120 compare to the one or more benchmark values 220 and the one or more outcome goal values 214. For instance, the goal tracker bar 900 can include an interval identifier 902 to indicate the monitoring period for the goal tracker bar 900 information (e.g., by month and year). The goal tracker bar 900 can also include a days remaining indicator 904 as a number showing how many days remaining for the monitoring period. A data tracker 906 can visually indicate a percentage of transmission data 118 that has been received out of a total amount of transmission data required for the monitoring period. Furthermore, the goal tracker bar 900 can include one or more physiological parameter data icons 908. The one or more physiological parameter data icons 908 can correspond to different physiological parameters being measured and can indicate whether or not the measured physiological parameter(s) 120 are within or outside the benchmark range (e.g., above or below the one or more benchmark values 220) with a simple visual indication. The physiological parameter data icons 908 can be colored red to indicate the measured physiological parameter(s) 120 being outside the benchmark range, and can be colored green or gray to indicate the measured physiological parameter(s) 120 being within the benchmark range. The goal tracker bar 900 can also include a last transmission timer 910 to present an amount of time that has elapsed since the last transmission data 118 was received. The visual indicators of the goal tracker bar 900 result in an improved clinic UI 124 by distilling the various data types being monitored and generated by the device management platform 102 into intuitive visualizations, which can be understood quickly by clinic personnel (e.g., even with minimal training), improving efficiency of the workflow 112.

Figure 10:
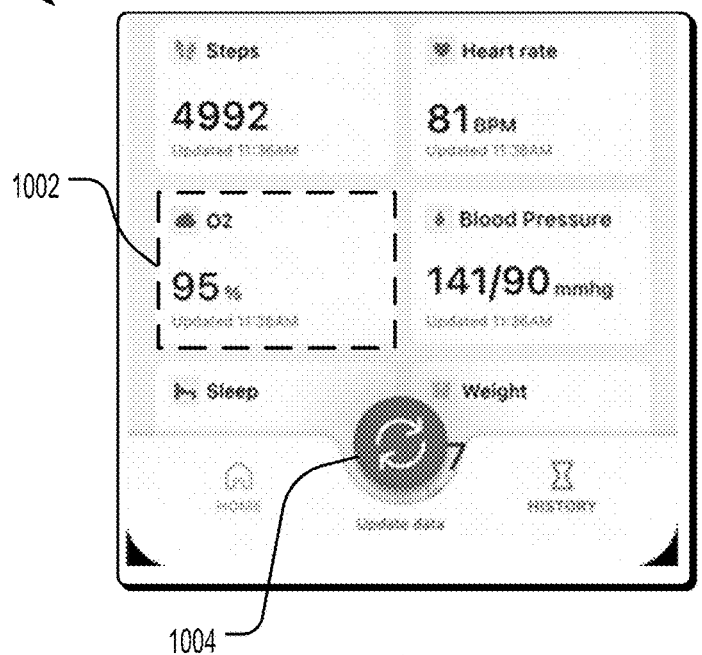
FIG. 10 illustrates an example system for managing patient devices using a parameter status interface of a patient user interface, which can form at least a portion of the system of FIG. 1.

FIG. 10 depicts a physiological parameter status interface 1000 which can form at least a part of the patient UI 216. The physiological parameter status interface 1000 can be presented at the secondary device 116 such as a mobile phone executing an application of the device management platform 102. The physiological parameter status interface 1000 can include one or more physiological parameter tiles 1002 corresponding to the measured physiological parameter(s) 120. The different physiological parameter tiles 1002 can present a current or latest value corresponding to the different measured physiological parameter(s) 120. Moreover, the one or more physiological parameter tiles 1002 can include latest update time stamp indicators. In some instances, the physiological parameter status interface 1000 includes a data update button 1004 which, upon receiving a user input, causes the patient system 114 (e.g., the secondary device 116) to send an updated transmission data 118 to the clinic system 106. The data update button 1004 can have a size (e.g., a diameter dimension in scenarios where the data update button 1004 is a circle) that is larger than other icons of the patient UI 216 (e.g., a home icon, a history icon, etc.) to give the data update button 1004 a prominent visual presentation. In some instances, the user input is received at the data update button 1004 in response to receiving the action instructions 212 at the patient system 114.

Figure 11:
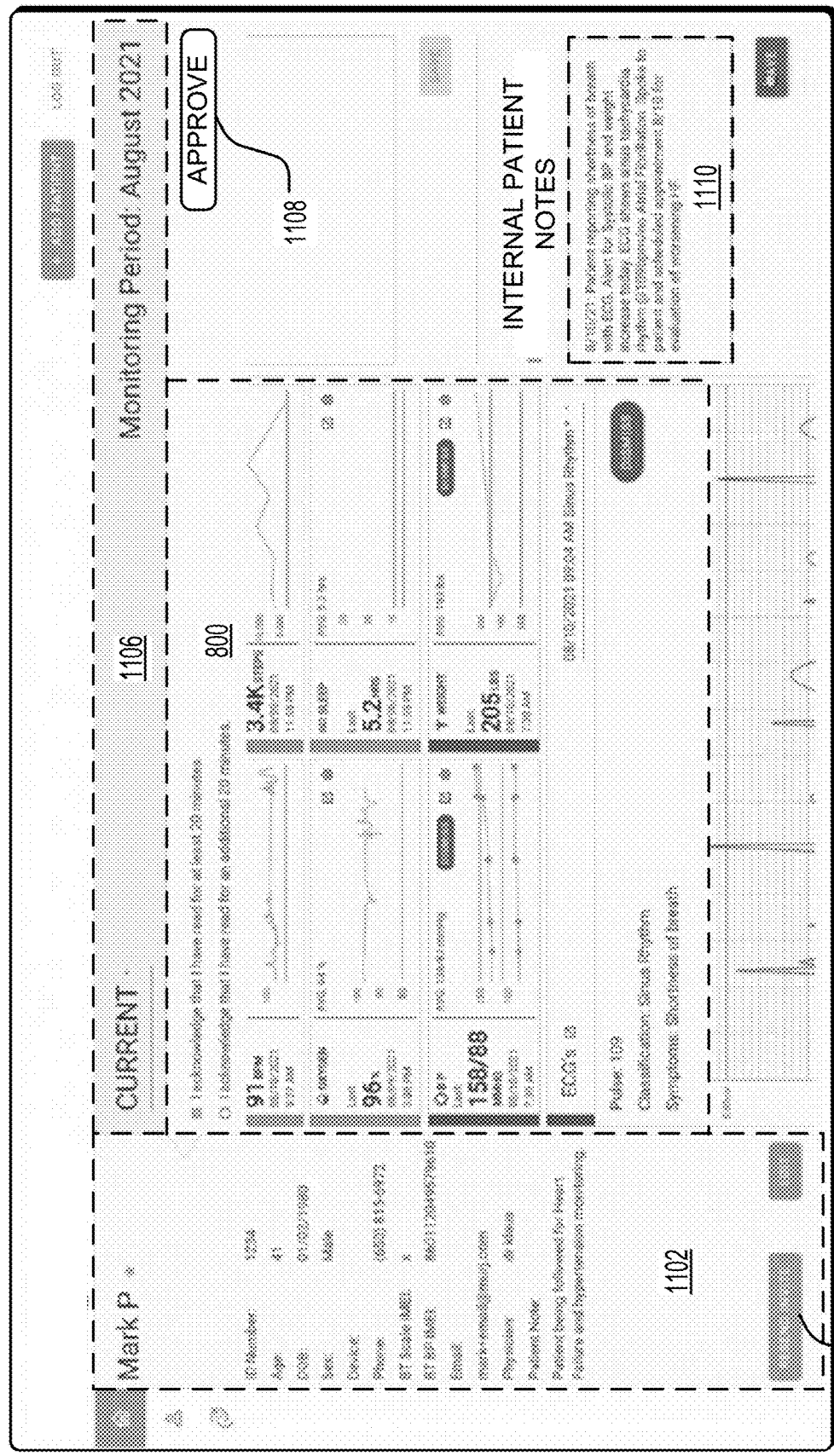
FIG. 11 illustrates an example system for managing patient devices using a workflow interface of a clinic user interface, which can form at least a portion of the system of FIG. 1.

FIG. 11 depicts a workflow interface 1100 to present features of the workflow 112, which can form at least a part of the clinic UI 124. The workflow interface 1100 can also include the monitoring interface section 800 and the goal tracker bar 900 discussed above.

For instance, the workflow interface 1100 can present the monitoring interface section 800 concurrently (e.g., simultaneously) with presenting a patient detail section 1102, for instance, as a side bar. The patient detail section 1102 can include a patient ID number, a patient age, a patient date of birth, a patient sex, a patient phone number, one or more device international mobile equipment identity (IMEI) identifiers (e.g., for the Bluetooth® scale, the Bluetooth® blood pressure device, etc.), a patient email address, a physician name assigned to the patient, and/or patient notes. The workflow interface 1100 can also include a resend invite button 1104 (e.g., at the patient detail section 1102 which, in response to an input, causes a message to be sent to the patient system 114 to initiate or re-initiate the onboarding procedure(s) 108). The patient detail section 1102 can also include an edit button to provide modifications to the patient details presented in the patient detail section 1102. In some examples, the patient details can include various timelines showing interventions (e.g., action instructions 212), so that the impact of such interventions on the measured physiological parameter(s) 120 is visually presented.

In some instances, the workflow interface 1100 includes a monitoring period label section 1106 to indicate if the monitoring period being presented at the workflow interface 1100 is the current monitoring period and/or a month and year of the monitoring period. The workflow interface 1100 can also include an approve button 1108 to receive an input indicating that clinic personnel has reviewed the information presented at the workflow interface 1100 and approves the monitoring period for billing (e.g., to initiate operations of the billing pathway 226). Moreover, the workflow interface 1100 can include an internal patient notes section 1110 to receive inputs generating clinic notes for the patient and/or the monitoring period which are only accessible by the clinic system 106.

In some examples, the analytics and reporting process 302 can be performed by the device management platform 102, the results of which can be presented at the clinic UI 124 (e.g., the workflow interface 1100). For instance, the device management platform 102 can analyze historical data to determine that a group of patients have a common or same outcome goal value 214, device types or device parameters for individual patients of the groups of patient (e.g., the technology tiers of the patients in the group of patients), and which device types or device parameters correlate to a higher likelihood of reaching the outcome goal value 214. Furthermore, the device management platform 102 can detect clinic actions occurring at the clinic system 106 and/or the clinic UI 124 and clinic action characteristics. For instance, the device management platform 102 can determine a duration of time that a portion of the clinic UI 124 (e.g., the workflow interface 1100) is viewed, a sequence in which features of the clinic UI 124 are interacted with, and the like.

Furthermore, the device management platform 102 can compare outcome results and device capabilities/secondary device 116 (e.g., technology tiers) of patients having a particular care plan or care pathway 210 (e.g., the heart failure pathway 518), thus determining correlations between types of devices and success rates (e.g., and/or medication consumption rates). For instance, the device management platform 102 may determine that patients using a smart watch have a higher likelihood of reaching the outcome goal values 214 and/or a higher likelihood of consistent medication consumption.

In some examples, the device management platform 102 can include an intervention tracker which can track and/or analyze interventions (e.g., action instructions 212) throughout the duration of the care plan. The intervention tracker can interface with an Electronic Healthcare Record (EHR) to receive, from the EHR, indications of any medication changes of the patient (e.g., automatically). The intervention tracker can adjust the one or more benchmark values 220 to reflect an expected change in a physiological parameter corresponding to the medication. The intervention tracker can track phone calls with the patient as well. Moreover, the device management platform 102 can track whether the patient is active or not and if the patient experiences any lifestyle activity changes, stress factor changes, or hospitalizations.

Figure 12:
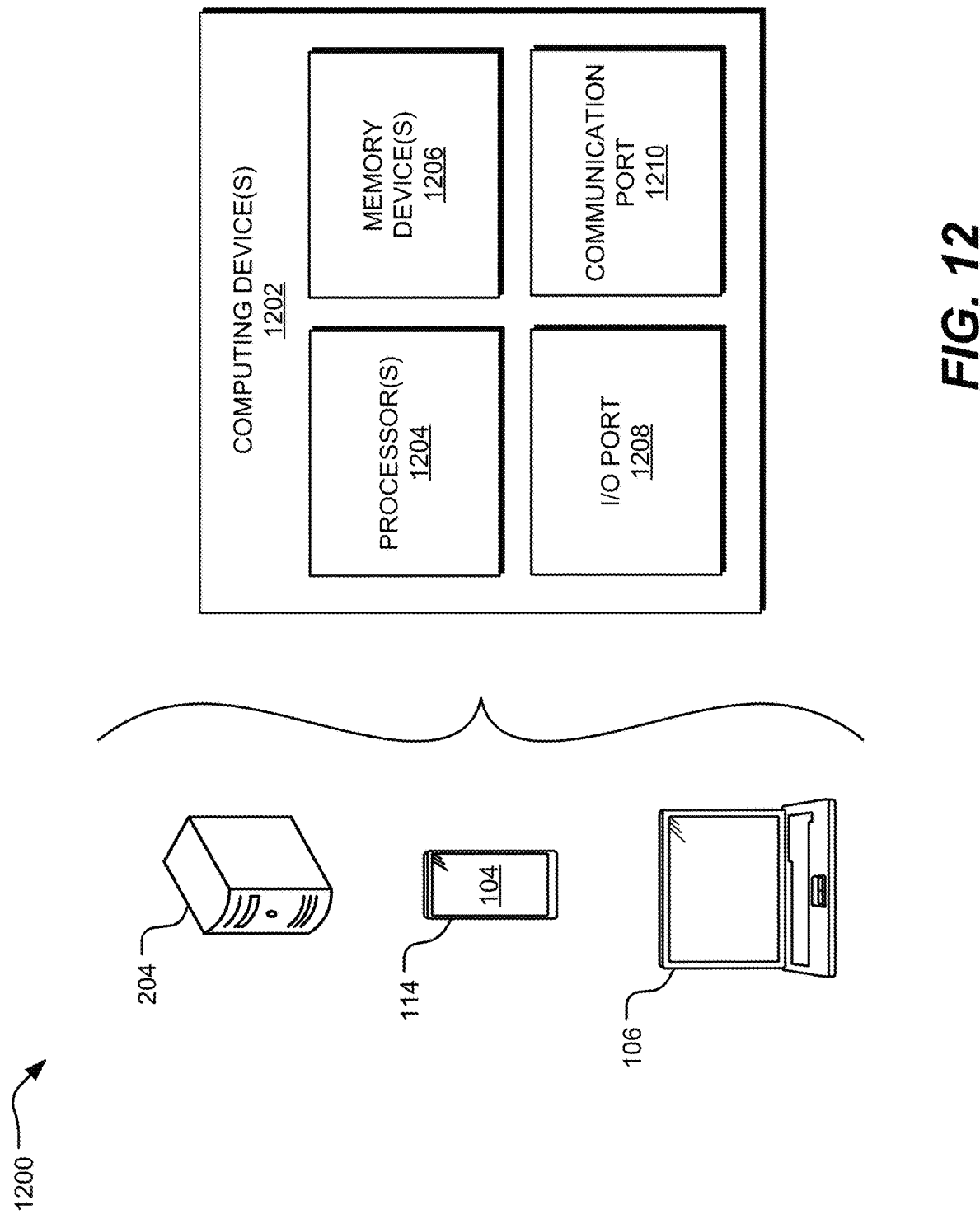
FIG. 12 illustrates an example system for managing patient devices using one or more computing systems, which can form at least a portion of the system of FIG. 1.

FIG. 12 illustrates an example system 1200 to provide the device management platform 102 which can include one or more computer system(s) 1202 which implement the systems 100-800 and the interfaces 900-1100 discussed herein. In one implementation, the one or more computing device(s) 1202 include the devices of the clinic system 106, the patient system 114 (e.g., the patient device 104, the secondary device 116, etc.), the one or more servers 204, and/or the database(s) 202.

In some instances, the computing device(s) 1202 includes a computer, a personal computer, a desktop computer, a laptop computer, a terminal, a workstation, a cellular or mobile phone, a mobile device, a smart mobile device a tablet, a wearable device (e.g., a smart watch, smart glasses, a smart epidermal device, etc.) a multimedia console, a television, an Internet-of-Things (IoT) device, a smart home device, a medical device, a virtual reality (VR) or augmented reality (AR) device, and/or the like. The computing device(s) 1202 may be integrated with, form a part of, or otherwise be associated with the systems 100-800 and interfaces 900-1100. It will be appreciated that specific implementations of these devices may be of differing possible specific computing architectures not all of which are specifically discussed herein but will be understood by those of ordinary skill in the art.

The computing device 1202 may be a computing system capable of executing a computer program product to execute a computer process. The device management platform 102 can be stored and executed at the computing device 1202 (e.g., as one or more software components). Data and program files may be input to the computing device 1202 (e.g., the transmission data 118 including the measured physiological parameter(s) 120, clinician inputs setting the one or more outcome goal values 214, the outcome goal date 218, the one or more benchmark values 220, the benchmark dates 222, and the like), which can read the files and executes the programs therein to generate the workflow 112 (e.g., the care pathways 210, the billing pathway 226, the care plans, etc.). Some of the elements of the computing device 1202 include one or more hardware processors 1204, one or more memory devices 1206, and/or one or more ports, such as input/output (IO) port(s) 1208 and communication port(s) 1210. Additionally, other elements that will be recognized by those skilled in the art may be included in the computing device 1202 but are not explicitly depicted in FIG. 12 or discussed further herein. Various elements of the computing device 1202 may communicate with one another by way of the communication port(s) 1210 and/or one or more communication buses, point-to-point communication paths, or other communication means.

The processor 1204 may include, for example, a central processing unit (CPU), a microprocessor, a microcontroller, a digital signal processor (DSP), and/or one or more internal levels of cache. There may be one or more processors 1204, such that the processor 1204 comprises a single central-processing unit, or a plurality of processing units capable of executing instructions and performing operations in parallel with each other, commonly referred to as a parallel processing environment.

The computing device 1202 may be stand-alone computer, a distributed computer, or any other type of computer, such as one or more external computers made available via a cloud computing architecture. The presently described technology is optionally implemented in software stored on the data storage device(s) such as the memory device(s) 1206, and/or communicated via one or more of the ports 1208 and 110, thereby transforming the computing device 1202 in FIG. 12 to a special purpose machine for implementing the operations described herein. Moreover, the unconventional arrangement of the one or more computing devices 1202 into the clinic system 106 and the patient system 114 (e.g., including the patient device 104 and the secondary device 116), as discussed herein, improves the fields of technology of implantable cardiac devices and implantable cardiac device monitoring software.

The one or more memory device(s) 1206 may include any non-volatile data storage device capable of storing data generated or employed within the computing device 1202, such as computer-executable instructions for performing a computer process, which may include instructions of both application programs and an operating system (OS) that manages the various components of the computing device 1202. The memory device(s) 1206 may include, without limitation, magnetic disk drives, optical disk drives, solid state drives (SSDs), flash drives, and the like. The memory device(s) 1206 may include removable data storage media, non-removable data storage media, and/or external storage devices made available via a wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, SSDs, and the like. The one or more memory device(s) 1206 may include volatile memory (e.g., dynamic random-access memory (DRAM), static random-access memory (SRAM), etc.) and/or non-volatile memory (e.g., read-only memory (ROM), flash memory, etc.).

Computer program products containing mechanisms to effectuate the systems and methods in accordance with the presently described technology may reside in the memory device(s) 1206 which may be referred to as machine-readable media. It will be appreciated that machine-readable media may include any tangible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

In some implementations, the computing device 1202 includes one or more ports, such as the I/O port 1208 and the communication port 1210, for communicating with other computing, network, or vehicle devices. It will be appreciated that the I/O port 1208 and the communication port 1210 may be combined or separate and that more or fewer ports may be included in the computing device 1202.

The I/O port 1208 may be connected to an I/O device, or other device, by which information is input to or output from the computing device 1202. Such I/O devices may include, without limitation, one or more input devices, output devices, and/or environment transducer devices.

In one implementation, the input devices convert a human-generated signal, such as, human voice, physical movement, physical touch or pressure, and/or the like, into electrical signals as input data into the computing device 1202 via the I/O port 1208. Similarly, the output devices may convert electrical signals received from the computing device 1202 via the I/O port 1208 into signals that may be sensed as output by a human, such as sound, light, and/or touch. The input device may be an alphanumeric input device, including alphanumeric and other keys for communicating information and/or command selections to the processor 1204 via the I/O port 1208. The input device may be another type of user input device including, but not limited to: direction and selection control devices, such as a mouse, a trackball, cursor direction keys, a joystick, and/or a wheel; one or more sensors, such as a camera, a microphone, a positional sensor, an orientation sensor, an inertial sensor, and/or an accelerometer; and/or a touch-sensitive display screen ("touchscreen"). The output devices may include, without limitation, a display, a touchscreen, a speaker, a tactile and/or haptic output device, and/or the like. In some implementations, the input device and the output device may be the same device, for example, in the case of a touchscreen.

In one implementation, the communication port 1210 is connected to the network 206 and the computing device 1202 may receive network data useful in executing the methods and systems set out herein as well as transmitting information and network configuration changes determined thereby. Stated differently, the communication port 1210 connects the computing device 1202 to one or more communication interface devices configured to transmit and/or receive information between the computing device(s) 1202 and other computing device(s) 1202 by way of one or more wired or wireless communication networks or connections. Examples of such networks or connections include, without limitation, Universal Serial Bus (USB), Ethernet, Wi-Fi, Bluetooth®, Near Field Communication (NFC), and so on. One or more such communication interface devices may be utilized via the communication port 1210 to communicate one or more other machines, either directly over a point-to-point communication path, over a wide area network (WAN) (e.g., the Internet), over a local area network (LAN), over a cellular network (e.g., third generation (3G), fourth generation (4G), Long-Term Evolution (LTE), fifth generation (5G), etc.) or over another communication means. Further, the communication port 1210 may communicate with an antenna or other link for electromagnetic signal transmission and/or reception.

In an example implementation, device management platform 102 may be embodied by instructions stored on the memory devices 1206 and executed by the processor 1204.

The system 1200 set forth in FIG. 12 includes but one possible example of a computing device 1202 that may employ or be configured in accordance with aspects of the present disclosure. It will be appreciated that other non-transitory tangible computer-readable storage media storing computer-executable instructions for implementing the presently disclosed technology on a computing system may be utilized. In the present disclosure, the methods disclosed may be implemented as sets of instructions or software readable by the computing device 1202.

Figure 13:
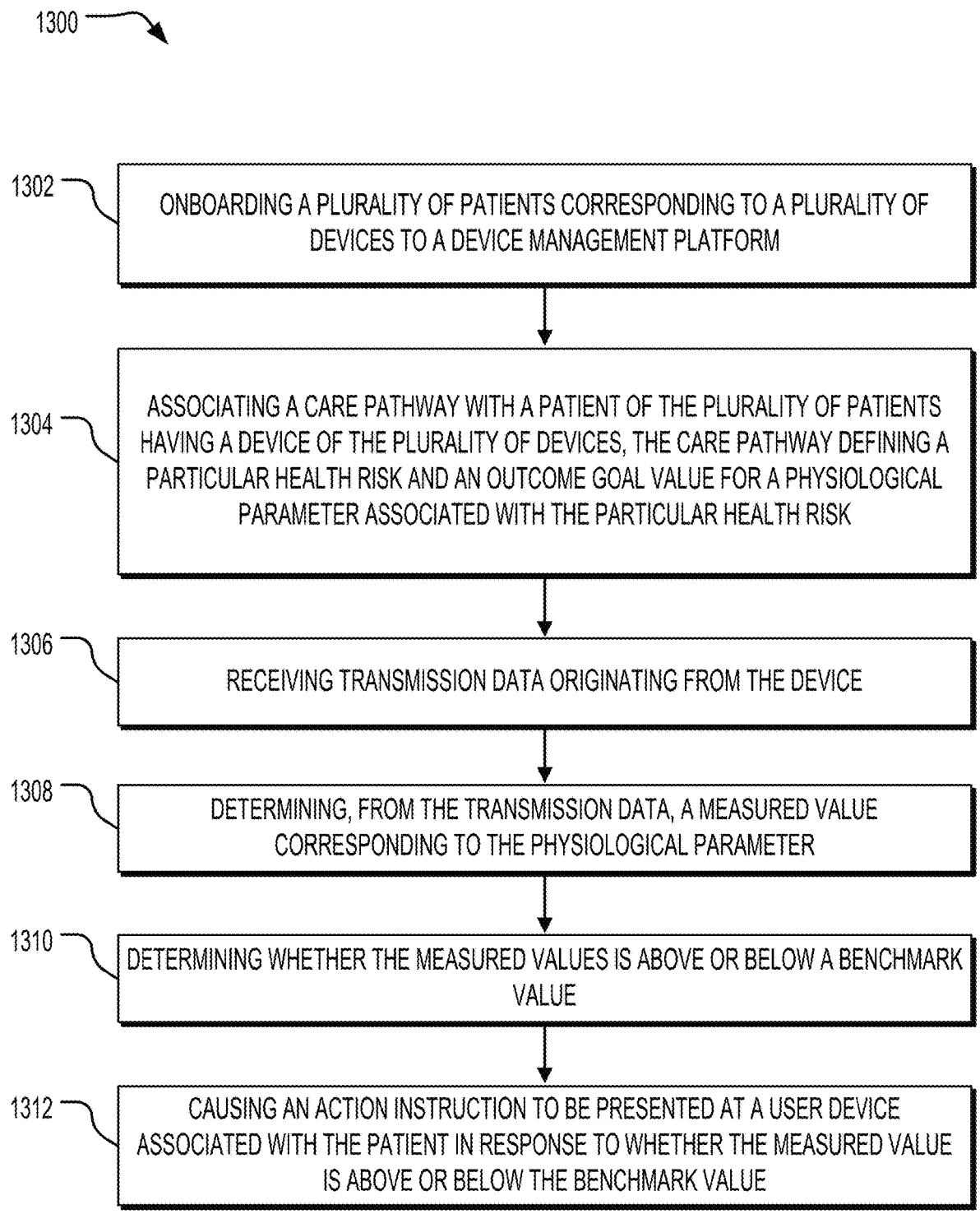
FIG. 13 illustrates an example method for managing patient devices with the device management platform, which can be performed by the system of FIG. 1.

FIG. 13 illustrates an example method 1300 to manage one or more patient devices 104 using the device management platform 102, which can be performed by any of the systems 100-800 or 1200 or presented at any of the interfaces 900-1100.

In some examples, at operation 1302, the method 1300 onboards a plurality of patients corresponding to a plurality of patient devices to a device management platform. At operation 1304, the method 1300 associates a care pathway with a patient of the plurality of patients having a patient device of the plurality of patient devices, the care pathway defining a particular health risk and an outcome goal value for a physiological parameter associated with the particular health risk. At operation 1306, the method 1300 receives transmission data originating from the patient device. At operation 1308, the method 1300 determines, from the transmission data, a measured value corresponding to the physiological parameter. At operation 1310, the method 1300 determines whether the measured values is above or below a benchmark value. At operation 1312, the method 1300 causes an action instruction to be presented at a user device associated with the patient in response to whether the measured value is above or below the benchmark value.

It is to be understood that the specific order or hierarchy of steps in the method 1300 depicted in FIG. 13, and throughout this disclosure, are instances of example approaches and can be rearranged while remaining within the disclosed subject matter. For instance, any of the operations depicted in FIG. 13 or throughout this disclosure may be omitted, repeated, performed in parallel, performed in a different order, and/or combined with any other of the operations depicted in FIG. 13 or throughout this disclosure.

While the present disclosure has been described with reference to various implementations, it will be understood that these implementations are illustrative and that the scope of the present disclosure is not limited to them. Many variations, modifications, additions, and improvements are possible. More generally, implementations in accordance with the present disclosure have been described in the context of particular implementations. Functionality may be separated or combined differently in various implementations of the disclosure or described with different terminology. These and other variations, modifications, additions, and improvements may fall within the scope of the disclosure as defined in the claims that follow.

What is claimed is:

1. A method to manage patient devices, the method comprising:
    associating, using one or more processors of a computing device, a care pathway with a patient having a patient device, the care pathway defining:
        a particular health risk and an outcome goal value for a physiological parameter associated with the particular health risk;
        an outcome goal date associated with the outcome goal value; and
        one or more benchmark dates corresponding to one or more one or more benchmark values of the physiological parameter, the one or more benchmark dates and one or more benchmark values being based at least partly on the outcome goal value and the outcome goal date;
    receiving, using a wireless transmission interface, transmission data originating from the patient device;
    determining, from the transmission data, a measured value corresponding to the physiological parameter;
    determining whether the measured value is above or below a benchmark value of the one or more benchmark values;
    generating an intervention in response to whether the measured value is above or below the benchmark value; and
    causing the intervention to be presented at a user device associated with the patient.

2. The method of claim 1, wherein the user device is a mobile device that captures the transmission data from the patient device and transmits the transmission data to a device management platform device remote from the mobile device.

3. The method of claim 1, wherein the care pathway is defined by one or more billing codes as one or more of:
    a remote patient monitoring pathway;
    a chronic care management pathway;

a primary care management pathway;
a transitional care management pathway;
a remote therapy monitoring pathway; or
a heart failure pathway.

4. The method of claim 1, wherein the physiological parameter is one or more of:
an amount of a physical activity;
a heart rate;
an amount of a sleep activity;
a blood oxygen saturation; or
an electrocardiogram (ECG) measurement.

5. The method of claim 1, wherein the transmission data is first transmission data from a first device being the user device, and further comprising receiving second transmission data from a second device, the second transmission data including:
a measured weight value;
a measured blood pressure value;
a measured glucose value; or
a measured temperature value.

6. The method of claim 5, wherein the second device is:
a Bluetooth device to send the second transmission data to the user device for transmission to a device management platform device; or
a cellular device to send the second transmission data to the device management platform device.

7. The method of claim 1, further comprising:
determining that a monitoring period, associated with one or more of a first benchmark date of the one or more benchmark dates or the outcome goal date, has completed;
receiving a clinician input, at a clinic user interface (UI), corresponding to the monitoring period that has completed; and
generating, in response to the clinician input, a report for the monitoring period.

8. The method of claim 7, wherein the monitoring period is based on one or more of a Current Procedural Terminology (CPT) billing code.

9. The method of claim 7, wherein the clinician input is a first clinician input and further comprising:
receiving, at the clinic UI, a second clinician input indicating whether the monitoring period is a 30-day monitoring period or a calendar month monitoring period.

10. The method of claim 1, further comprising determining a medication consumption date associated with the patient, wherein:
the transmission data is received after the medication consumption date; and
the benchmark value is at least partly based on the medication consumption date.

11. A method to manage a patient device, the method comprising:
associating, using one or more processors of a computing device, a care pathway with a patient having the patient device based on a clinician input received at a clinic user interface (UI), the care pathway defining:
a particular health risk associated with one or more physiological parameters; and
one or more predetermined threshold values corresponding to the one or more physiological parameters;
receiving, using a wireless transmission interface, transmission data originating from the patient device;
determining, from the transmission data, a measured value corresponding to a physiological parameter of the one or more physiological parameters;
determining whether the measured value is above or below a predetermined threshold value of the one or more predetermined threshold values;
presenting an indication of whether the measured value is above the predetermined threshold value at the clinic UI;
generating an intervention in response to whether the measured value is above or below the predetermined threshold value; and
causing the intervention to be presented at a patient UI displayed at a user device associated with the patient.

12. The method of claim 11, wherein the intervention indicates an amount of steps to be walked for a number of one or more days.

13. The method of claim 11, wherein the clinician input is a first clinician input, and further comprising:
receiving a second clinician input at the clinic UI indicating the predetermined threshold value;
storing the predetermined threshold value at a device management platform storage device in response to the second clinician input; and
retrieving the predetermined threshold value from the device management platform storage device to determine whether the measured value is above or below the predetermined threshold value.

14. The method of claim 13, further comprising receiving a third clinician input at the clinic UI in response to presenting the indication of whether the measured value is above the predetermined threshold value, causing the intervention to be presented at the patient UI is in response to the third clinician input.

15. The method of claim 13, further comprising receiving an updated data transmission in response to causing the intervention to be presented at the patient UI.

16. A method to manage a patient device, the method comprising:
associating, using one or more processors of a computing device, a plurality of care pathways with a plurality of patients having a plurality of patient devices, a care pathway of the plurality of care pathways defining:
a particular health risk for a patient of the plurality of patients, the particular health risk being associated with one or more physiological parameters; and
one or more predetermined threshold values corresponding to the one or more physiological parameters;
receiving, using a wireless transmission interface, transmission data originating from the plurality of patient devices;
receiving, at a clinic user interface (UI), a first clinician input selecting a patient identifier corresponding to the patient;
determining, from the transmission data and in response to the first clinician input, a measured value corresponding to a physiological parameter of the one or more physiological parameters for the patient;
presenting, at the clinic UI, an indication of whether the measured value is above or below a predetermined threshold value of the one or more predetermined threshold values;
generating an intervention in response to a second clinician input at the clinic UI; and
causing the intervention to be presented at a patient UI displayed at a user device associated with the patient.

17. The method of claim 16, wherein the intervention is a first intervention, and further comprising:
determining user device parameters of the user device associated with the patient;

determining that the user device parameters fail to satisfy a device requirement associated with the care pathway; and causing, in response to the user device parameters failing to satisfy the device requirement, one or more of:

a second intervention to be presented at the patient UI displayed at the user device; or a supplemental device to be shipped to a physical address associated with the patient identifier.

18. The method of claim 16, further comprising:

receiving, a third clinician input at the clinic UI; and presenting, in response to the third clinician input, a patient profile including two or more of:

a device type or parameter of the user device;

the care pathway associated with the patient;

a device requirement associated with the physiological parameter defined by the care pathway;

a latest measured value associated with an outcome goal; or an indication of whether the measured value is greater than a benchmark value.

19. The method of claim 16, further comprising:

determining a Current Procedural Terminology (CPT) billing code associated with the care pathway;

determining a monitoring period associated with the CPT billing code, the one or more predetermined threshold values including a benchmark value for the monitoring period;

determining a data transmission schedule corresponding to the monitoring period; and causing the user device to transmit the transmission data according to the data transmission schedule.

20. The method of claim 19, wherein the CPT billing code is a first CPT billing code, and further comprising:

determining that clinician activity or a data transmission fails to satisfy a first requirement of the first CPT billing code for the monitoring period; and in response to the clinician activity or the data transmission failing to satisfy the first requirement of the first CPT billing code, determining that the clinician activity or the data transmission satisfies a second requirement of a second CPT billing code for the monitoring period; and generating a report corresponding to the second CPT billing code instead of the first CPT code for the monitoring period.

\* \* \* \* \*